(12) United States Patent
White et al.

(10) Patent No.: US 8,275,449 B2
(45) Date of Patent: Sep. 25, 2012

(54) OVERLAY IMAGE CONTRAST ENHANCEMENT

(75) Inventors: Christopher A. White, Toronto (CA);
Desmond Hirson, Thornhill (CA);
Stanley Poon, Thornhill (CA); James Mehi, Thornhill (CA)

(73) Assignee: VisualSonics Inc., Toronto (CA)

( * ) Notice: Subject to any disclaimer, the term of this patent is extended or adjusted under 35 U.S.C. 154(b) by 887 days.

(21) Appl. No.: 11/595,047

(22) Filed: Nov. 10, 2006

(65) Prior Publication Data

US 2007/0238954 A1 Oct. 11, 2007

Related U.S. Application Data

(60) Provisional application No. 60/735,399, filed on Nov. 11, 2005.

(51) Int. Cl.
*A61B 6/00* (2006.01)
(52) U.S. Cl. ........................................................ 600/431
(58) Field of Classification Search ................... 600/431
See application file for complete search history.

(56) References Cited

U.S. PATENT DOCUMENTS

| | | | |
|---|---|---|---|
| 5,316,771 A | 5/1994 | Barenholz et al. | |
| 6,226,415 B1 * | 5/2001 | Wilson et al. | 382/275 |
| 6,264,917 B1 | 7/2001 | Klaveness et al. | |
| 6,705,992 B2 | 3/2004 | Gatzke | |
| 6,837,855 B1 | 1/2005 | Puech | |
| 6,851,392 B2 | 2/2005 | Zan et al. | |
| 7,052,460 B2 | 5/2006 | Liu et al. | |
| 7,133,713 B2 | 11/2006 | Zan | |
| 7,139,676 B2 | 11/2006 | Barford | |
| 7,255,678 B2 | 8/2007 | Mehi et al. | |
| 2004/0126321 A1 * | 7/2004 | Quay | 424/9.52 |
| 2004/0167395 A1 * | 8/2004 | Behrenbruch et al. | 600/420 |
| 2005/0089218 A1 * | 4/2005 | Chiba | 382/165 |
| 2005/0197543 A1 | 9/2005 | Zan et al. | |
| 2006/0078501 A1 | 4/2006 | Goertz et al. | |
| 2007/0081700 A1 * | 4/2007 | Blumenfeld et al. | 382/128 |
| 2007/0081701 A1 * | 4/2007 | Sirohey et al. | 382/128 |
| 2007/0239001 A1 | 10/2007 | Mehi et al. | |

FOREIGN PATENT DOCUMENTS

| WO | WO 01/68150 A1 | 9/2001 |
| WO | WO 2007/058895 A2 | 5/2007 |

OTHER PUBLICATIONS

Villanueva et al., "Microbubbles Targeted to Intracellular Adhesion Molecule-1 Bind to Activated Coronary Artery Endothelial Cells," *Circulation* (1998) 98: 1-5.

Weller et al., "Modulating Targeted Adhesion of an Ultrasound Contrast Agent to Dysfunctional Endothelium," *Ann. Biomed. Engineering*, (2002) 30: 1012-1019.

Singbartl K, Green SA, Ley K. (2000) "Blocking P-selectin protects from ischemia/reperfusion induced acute renal failure" FASEB J. 14: 48-54.

* cited by examiner

*Primary Examiner* — Tse Chen
*Assistant Examiner* — Hien Nguyen
(74) *Attorney, Agent, or Firm* — Fenwick & West LLP

(57) ABSTRACT

A method of creating an image difference overlay comprises identifying a loop of reference images of a subject and identifying a loop of data images of the subject. The loop of image data can be identified after an event, such as the administration of contrast agent to the subject. A reference loop image frame is compared to one or more data loop image frames and the reference loop frame is associated with a data loop image frame which closely resembles the data loop image frame. Each of the associated frames can then be processed and used to create an image difference overlay frame.

57 Claims, 23 Drawing Sheets

OVERLAY IMAGE CONTRAST ENHANCEMENT

CROSS REFERENCE TO RELATED APPLICATIONS

This application claims the benefit of U.S. Provisional Patent Application No. 60/735,399 filed Nov. 11, 2005, which is fully incorporated herein and made apart hereof.

BACKGROUND

Sufficient contrast differences between tissues in acquired images of patients and small animals are important for medical diagnosis and biomedical research. To increase the signal intensity difference between tissues in such acquired images contrast agents specific for that imaging modality are often used. A comparison between a single post-contrast agent administrated image with a single pre-contrast agent image, as selected by the operator, can be made to identify specific tissue volumes that have undergone contrast enhancement. Identification of which tissues undergo contrast enhancement, and how much enhancement, is an important indicator for many biomedical research and diagnostic applications. For in vivo imaging, however, respiration, cardiac, and non-specific motion of patients and small animals causes post-contrast injection images to be dissimilar when compared to a pre-single injection image making the comparison difficult.

SUMMARY OF THE INVENTION

A method of creating an image difference overlay, or enhanced medical image, comprises identifying a set of reference images, or frames, of a subject and identifying a set of data images, or frames, of the subject. A set of images, also referred to as a "loop" or "cine clip" can comprise one or more images acquired sequentially. The set of data images can be identified after an event, such as the administration of contrast agent to the subject, or after removal of a contrast agent already in the subject. A single reference image can be compared to one or more data set images and the reference set frame is associated with a data set image which closely resembles the reference set image. Each of the associated images can then be processed and used to create an enhanced medical image, also referred to throughout as an image difference overlay, or contrast overlay. In one non-limiting example, the contrast agent used is a microbubble contrast agent, and the image sets are acquired using ultrasound.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

FIG. 6D shows the data loop image of FIG. 6B with the contrast overlay of FIG. 6C blended in.

FIG. 7A shows kidney before injection and 7C shows the kidney after injection. Background-subtracted contrast enhancement after injection is shown in FIG. 7D. FIG. 7B shows pixel intensity averaged over a ROI encompassing the kidney for bolus injections of $10^5$, $10^6$, $10^7$, and $10^8$ micro bubbles (herein referred to as MB).

DETAILED DESCRIPTION

Figure 1:
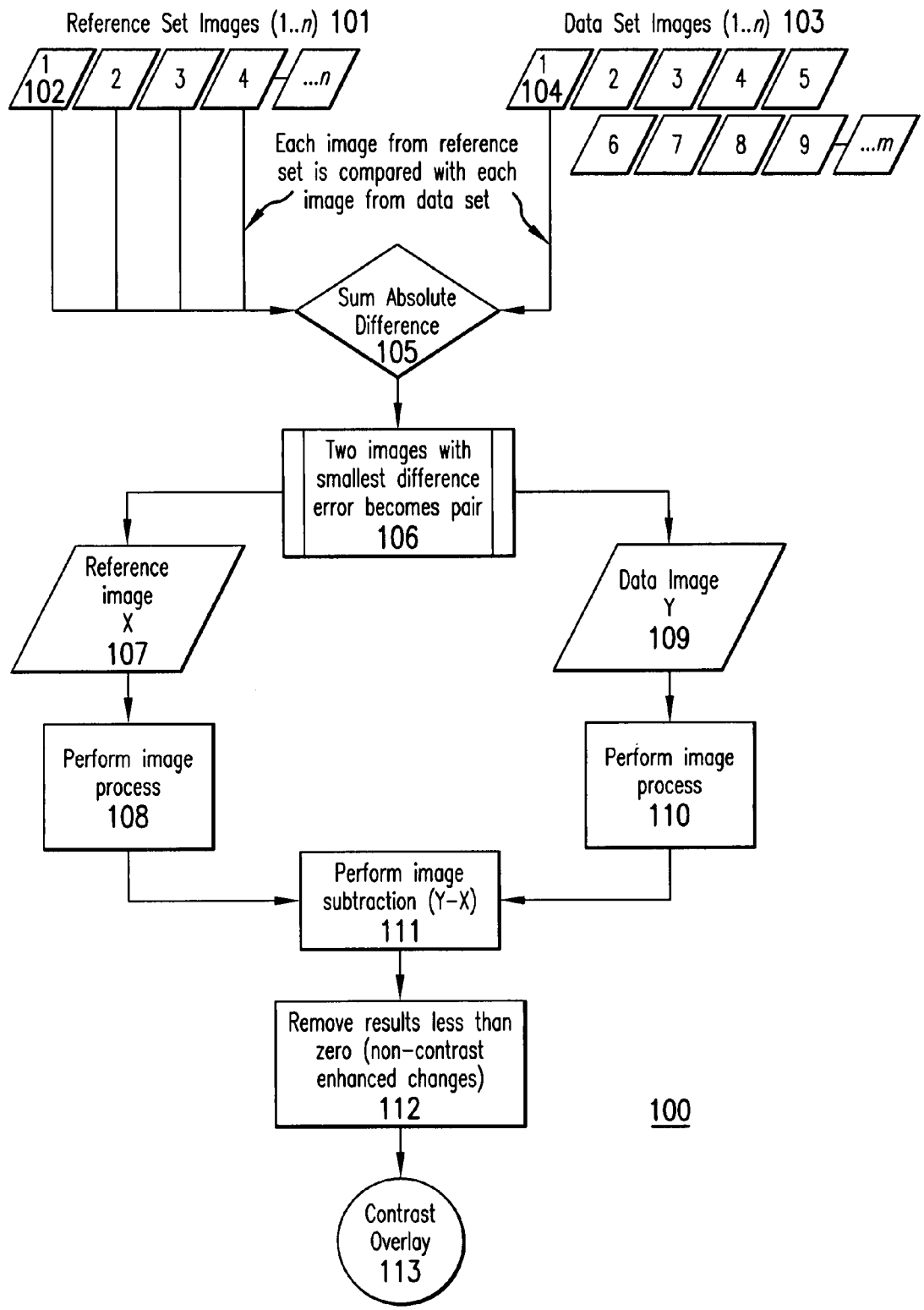
FIG. 1 is a flow diagram in block form of an exemplary embodiment of a method creating a contrast overlay.

The present invention may be understood more readily by reference to the following detailed description of preferred embodiments of the invention and the Examples included therein and to the Figures and their previous and following description.

Before the present compounds, compositions, articles, devices, and/or methods are disclosed and described, it is to be understood that this invention is not limited to specific synthetic methods, specific computer or imaging system architecture or modality or to particular contrast agent or administration protocols, as such may, of course, vary. It is also to be understood that the terminology used herein is for the purpose of describing particular aspects only and is not intended to be limiting.

As used throughout, the singular forms "a," "an" and "the" include plural referents unless the context clearly dictates otherwise. Thus, for example, reference to "a processor" can include two or more such processors unless the context indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

By a "subject" is meant an individual. The term subject includes small or laboratory animals as well as primates, including humans. A laboratory animal includes, but is not limited to, a rodent such as a mouse or a rat. The term laboratory animal is also used interchangeably with animal, small animal, small laboratory animal, or subject, which includes mice, rats, cats, dogs, fish, rabbits, guinea pigs, rodents, etc. The term laboratory animal does not denote a particular age or sex. Thus, adult and newborn animals, as well as fetuses (including embryos), whether male or female, are included. The term subject can also include other forms such as a collection of isolated cells either in vivo or ex vivo as might be collected on a Petri dish.

Provided herein are systems and methods for creating an enhanced medical image, also referred to herein as an image difference overlay or as a contrast overlay. Such terms are used interchangeable throughout the description, examples and in the claims. An enhanced medical image, or contrast overlay can be used to highlight differences in intensity between a reference image and a data image. A "reference image" is also referred to throughout as a "reference set image" and a "data image" is also referred to as a "data set image." Such terms are used interchangeably throughout.

In one aspect, the methods and systems described in this document illustrate an improved method for the identification and quantification of small brightness differences in a medically acquired image, or a medical image, as a result of infusion of contrast agent specific for that imaging modality.

When a contrast agent for a given imaging modality is used, multiple pre-injection images (reference set images) can be used as a reference set. In this way, the accuracy and simplicity of matching post-injection images (data set images) with similar pre-injection images from a set of multiple pre-injection images is increased. The results include reduced effort on the part of the operator, and improved accuracy in the results. As used herein, a pre-injection image, selected from a set of multiple pre-injection images, matched with a post-injection image, selected from a set of multiple post-injection image can be referred to as a contrast overlay or an enhanced medical image.

The process for image processing uses two or more sets of images: a reference set, and a post-injection or post increased contrast data set. The data set typically refers to a series of sequential images composed as a image loop, or cine clip. The position of the animal can be made as static as possible to prevent false positives. The methods described herein have inherent stability for small changes in image positioning due to respiration and cardiac motion, or due to other biodynamic cycle motions of a subject. The reference set or sets and data set or sets can then be compared with each other to associate the images(s) which are most similar. Each image of these associated loops can then be processed with filters to remove local image features and image noise. They can then be subtracted and a difference map generated to form a contrast overlay.

The described system and methods for processing the data enables more accurate results to be obtained without the need for complicated ECG or respiration gating. The systems and methods can also be used to image embryos in vivo where an accurate ECG signal specific to that embryo is not acquired. Heart beats and the respiration motion of a subject typically disturbs or moves the image disallowing direct image subtraction to highlight differences in intensity. Image subtraction is typically only suitable for comparing images where only the features of interest have changed. If the two images are dissimilar, have shifted or undergone some other transformation, the subtraction process will result in significant false results. The disclosed systems can also be used for perfusion imaging. Perfusion imaging can be performed by injecting contrast agent into the subject, allowing the agent to circulate and then destroying them in a destruction event. The time taken for the re-perfusion can be used to establish flow or perfusion into an organ or portion thereof.

An exemplary method for creating an image difference overlay comprises identifying a set of reference images of a subject or portion thereof. The method further comprises identifying a set of data images of the subject or the portion thereof. A data image can be compared to a plurality of images of the reference image loop. At least one data image can be associated with at least one reference image. An image subtraction on the associated images can be performed to produce the contrast overlay or enhanced medical image.

In one aspect, the data image is associated with the at least one reference loop image based on similarity. For example, the similarity can be determined by summing the absolute difference of pixel intensity levels and associating the data set image with the reference set image or images which yield the smallest absolute difference value. Other methods can be used to determine similarity.

The identification of a set of reference images and data images can comprise acquiring images using an imaging modality. The imaging modality used can be any medical imaging modality. For example, the imaging modality can selected from the group consisting of ultrasound, computed tomography (CT), optical coherence tomography (OCT), radiography (or X-Ray including fluorescence), optical detection (either with or without a magnifying lens or microscope), thermography, nuclear medical imaging, positron emission tomography, bioluminescent imaging, biofluorescent imaging, and magnetic resonance imaging (MRI).

The methods described herein can further comprise administering a contrast agent to the subject. The administered contrast agent is typically complementary to the imaging modality used. For example, a micro bubble (MB) contrast agent can be used with ultrasound imaging modalities. Contrast agents complementary to other imaging modalities are known to those skilled in the art.

A data set image can comprise data based on signals received from one or more contrast agent(s) located in the subject or a portion thereof. Image subtraction on the associated reference set images can be used to highlight the portion of the image corresponding to the location of the administered contrast agent in the subject.

In one aspect, the contrast agent can be administered to the subject subsequent to acquiring images of the reference set and the images of the data set can be acquired subsequent to the administration of the contrast agent.

In another aspect, the images of the data set can be acquired subsequent to the administration of the contrast agent and the images of the reference set are acquired subsequent to acquiring the images of the data set. The administered contrast agent can be substantially cleared from the subject prior to acquiring the images of the reference set. For example, the micro bubble contrast agent can be substantially cleared by destroying the contrast agent with ultrasound. Micro bubble contrast agent can also be destroyed via chemical interactions with other administered drugs and can also be destroyed by altering the oxygenation level of the blood. For example, increasing the percentage oxygen breathed to the subject can be used to increase the oxygen level in the blood. Methods to destroy or remove contrast agent for other modalities can include chemical methods or waiting until the contrast agent is expelled from the subject. Contrast agent expulsion from the subject can include being filtered by the liver and or kidneys or via the contrast agent breaking down or binding with other molecules and organelles already present in the subject including cells, oxygen, and carbon dioxide.

A system for creating a contrast overlay can comprises a processing unit or processor for identifying a set of reference images of a subject or portion thereof. The same or another processor or processing unit of the system can identify a set of data images of the subject or the portion thereof and can compare a reference image to a plurality of images of the data image set. Moreover, the same or another processing unit can associate at least one reference image with at least one data image and can performing an image subtraction on the associated images to produce the contrast overlay. The processing unit can comprise software or a computer readable medium having computer readable code for comparing reference set images to data set images and for subtracting reference set images from data set images.

Further provided herein is a computer-readable medium having computer readable program code for creating a contrast overlay. The computer readable medium comprises program code for inputting an identified loop of reference images of a subject or portion thereof. The computer-readable medium further comprises program code for inputting an identified set of data images of the subject or the portion thereof and program code for comparing a data image to a plurality of images of the reference image set and matching at least one data image with at least one reference image. The computer-readable medium also can comprise program code for performing an image subtraction on the matched images to produce the contrast overlay.

An exemplary method of creating a contrast overlay comprises identifying a set of reference images of a subject and identifying a set of data images of the subject. The set of data images, which includes a plurality of data set images, can be identified after an event, such as the administration of contrast agent to the subject or the removal of contrast agent from the subject either by destruction or by being expelled from the subject. A data set image is compared to one or more reference set images, which comprise a reference set, and the data set image is associated with one or more reference set images which closely resembles the data set image. The associated images can then be processed and used to create a contrast overlay image. In one non-limiting example, the contrast agent used is a microbubble contrast agent, and the images loop images are identified using ultrasound.

Also, provided herein is a method for creating an image difference overlay (also called herein a "contrast overlay" or "enhanced medical image") comprising the steps of identifying a set of reference images of a subject; identifying a set of data images of the subject; comparing a data set image to each reference set image wherein the data set image is associated with one or more reference set images which most closely resembles the data set image; performing optional image processing on each of the associated images; performing image subtraction of the associated data image with an associated reference image wherein an contrast overlay frame is created.

The reference set and data set can comprise a plurality of reference set and data set ultrasound images. The data set can comprise "after" ultrasound images. After images are images of the same subject, or portion thereof, as the reference images acquired before some event, such as the administration of a contrast agent in the subject or after the destruction of all or a portion of an administered contrast agent.

To obtain an ultrasound image with or without a contrast agent, high frequency ultrasound can be used. The methods described herein are not limited to ultrasound and ultrasound contrast agents however. Any imaging modality can be used with a complementary contrast agent. Moreover, if CT, Micro-CT, MRI, OTC, Bioluminescence, Biofluorescence, or another imaging modality is used, a complementary contrast agent can be selected as would be clear to one skilled in the art.

If ultrasound is used, the ultrasound can be transmitted into the subject at a frequency of about 15 megahertz (MHz) or greater. Lower frequency or clinical frequency ultrasound, however, can also be used. Thus, ultrasound can be transmitted into the subject at a frequency of less than 15 MHz.

Optionally, the ultrasound is transmitted into the subject at a frequency of between about and between 15 MHz and about 80 MHz. Thus, the ultrasound can be transmitted into the subject at a frequency of about and between 20 MHz, 30 MHz, 40 MHz, 50 MHz, 60 MHz, 70 MHz, 80 MHz, or higher. For example, the ultrasound can be transmitted into the subject at a frequency of about 100 MHz or higher.

If high frequency ultrasound is desired, the ultrasound for use with the disclosed methods can be applied, transmitted and received using an ultrasonic scanning device that can supply an ultrasonic signal of at least 15 MHz to the highest practical frequency. Any system capable of operating at such frequencies can be used. One such device is the VisualSonics™ (Toronto, Calif.) UBM system model VEVO™ 660.

Another device is the VisualSonics™ (Toronto, Calif.) model VEVO™ 770. Another device is the VisualSonics™ (Toronto, Calif.) model VEVO™ 770B. Another such system can have the following components as described in U.S. patent application Ser. No. 10/683,890, US patent application publication 20040122319, which is incorporated herein by reference. If clinical frequencies of less than 15 MHz are used, any ultrasound system capable of operating at clinical frequencies can be used.

Other devices capable of transmitting and receiving ultrasound at the desired frequencies can also be used. For example, ultrasound systems using arrayed transducers can be used. One such exemplary array system, which is incorporated herein by reference for its teaching of a high frequency array ultrasound system, is described in U.S. nonprovisional application Ser. No. 11/592,741 titled "HIGH FREQUENCY ARRAY ULTRASOUND SYSTEM" by James Mehi, Ronald E. Daigle, Laurence C. Brasfield, Brian Starkoski, Jerrold Wen, Kai Wen Liu, Lauren S. Pflugrath, F. Stuart Foster, and Desmond Hirson, and filed Nov. 2, 2006.

In one aspect, the ultrasound images can be high-resolution, high frequency ultrasound images wherein a contrast agent was injected into the subject.

Thus, the methods can comprise the administration of a contrast agent to a subject. If ultrasound is the imaging modality used, the contrast agent can be a microbubble contrast agent. A contrast agent such as a microbubble population for ultrasound imaging is only exemplary. Contrast agents for CT, Micro-CT, MRI, Optical Coherence, bioluminescence, bioflorescence, or other imaging modalities can also be used.

A microbubble contrast agent typically comprises a plurality of microbubbles. Non-limiting examples of commercial microbubble contrast agents include, but are not limited to, Definity™, Sonovue™, Levovist™, Optison™, MicroMarker™, and MicroMarker™ Depo™ Moreover, microbubbles can be obtained from Targeson (Charlottesville, Va.) or ImaRx (Tucson, Ariz.), Bracco (Amsterdam, Netherlands), and VisualSonics Inc. (Toronto, Calif.). Ultrasound contrast agents are typically gas filed bubbles with diameters ranging from 1 to 4 microns. The bubble size distribution can range form sub-micron size to up to 10 micron in size. An exemplary bubble produced by ImaRx bubble has an average size of 0.9 microns and an exemplary bubble from Targeson has a range of 2 to 4 microns in size. Another exemplary bubble product is the Depo™ MicroMarker™ product made by Bracco for VisualSonics. The Depo™ product comprises a larger bubble population that is designed to lodge in the small vasculature of a subject. The term microbubble as used herein is not intended to be limited to bubbles of 1 micron or larger. Nano-sized bubbles are also included in the term microbubble.

Thus, the methods and systems described herein are not limited to any particular contrast agent. Microbubble commercial contrast agents can be used, but one skilled in the art can also produce microbubbles that would be effective with the disclosed systems and methods. Combinations of microbubble populations can also be used. Such microbubbles can be targeted, untargeted or lodging microbubbles.

A typical microbubble contrast agent comprises a thin flexible or rigid shell composed of albumin, lipid or polymer confining a gas such as nitrogen or a perflurocarbon. Other examples of representative gases include air, oxygen, carbon dioxide, hydrogen, nitrous oxide, inert gases, sulpher fluorides, hydrocarbons, and halogenated hydrocarbons. Liposomes or other microbubbles can also be designed to encapsulate gas or a substance capable of forming gas as described in U.S. Pat. No. 5,316,771. In another embodiment, gas or a composition capable of producing gas can be trapped in a virus, bacteria, or cell to form a microbubble contrast agent. The described ultrasound contrast agents improve contrast by acting as sound wave reflectors due to acoustic differences between the agents and surrounding liquid or by resonating.

A wide variety of materials can be used in preparing microbubble membrane or shell. Any compound or composition that aids in the formation and maintenance of the bubble membrane or shell by forming a layer at the interface between the gas and liquid phases can be used. Sonication can be used for the formation of microbubbles, i.e., through an ultrasound transmitting septum or by penetrating a septum with an ultrasound probe including an ultrasonically vibrating hypodermic needle. Optionally, larger volumes of microbubbles can be prepared by direct probe-type sonicator action on the aqueous medium in which microbubbles are formed in the presence of gas (or gas mixtures) or another high-speed mixing technique, such as blending or milling/mixing. Other techniques such as gas injection (e.g. venturi gas injection), mechanical formation such as through a mechanical high shear 15 valve (or double syringe needle) and two syringes, or an aspirator assembly on a syringe, or simple shaking, may be used. Microbubbles can also be formed through the use of a liquid osmotic agent emulsion supersaturated with a modifier gas at elevated pressure introduced into in a surfactant solution.

Thus, the administered microbubbles can comprise one or more gasses. For example, the gas can be a fluorine containing hydrocarbon gas. Optionally, the gas is selected from the group consisting of decafluorobutane, octafluorobutane, perfluorohexane, and dodecofluoropentane. The gas can also be sulfur hexafluoride or nitrogen. The microbubbles are not limited to these gases, however, and other gases used for ultrasound contrast agents can also be used.

Non-limiting gases that can be used alone or in combination include, for example, air; nitrogen; oxygen; carbon dioxide; hydrogen; an inert gas such as helium, argon, xenon or krypton; a sulfur fluoride such as sulfur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. At least some of the halogen atoms in halogenated gases can be fluorine atoms; thus halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons. Representative perfluorocarbons include perfluoroalkanes such as perfluoromethane, perfluoroethane, perfluoropropanes, perfluorobutanes (e.g. perfluoro-n-butane, optionally in admixture with other isomers such as perfluoro-isobutane), perfluoropentanes, perfluorohexanes or perfluoroheptanes; perfluoroalkenes such as perfluoropropene, perfluorobutenes (e.g. perfluorobut-2-ene), perfluorobutadiene, perfluoropentenes (e.g. perfluoropent-1-ene) or perfluoro-4-methylpent-2-ene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane or perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes, perfluoropentanes and perfluorohexanes, can be particularly advantageous in view of the recognized high stability in the bloodstream of microbubbles containing such gases. Other gases with physicochemical characteristics which cause them to form highly stable microbubbles in the bloodstream may likewise be useful.

Thus, in one aspect, one or more gasses can be enclosed in a shell to form a microbubble. The shell can comprise a lipid. Optionally, the shell is a lipid monolayer and the gas is decafluorobutane.

A contrast agent can be modified to achieve a desired volume percentage by a filtering process, such as by microfiltration using a porous membrane. Contrast agents can also be modified by allowing larger bubbles to separate in solution relative to smaller bubbles. For example, contrast agents can be modified by allowing larger bubbles to float higher in solution relative to smaller bubbles. A population of microbubbles of an appropriate size to achieve a desired size distribution can subsequently be selected. Other means are available in the art for separating microbubble sizes and can be adapted to select a microbubble population of bubbles such as by centrifugation. Thus, microbubble populations can be produced with a proportion of bubbles large enough to lodge in the microvasculature of a subject. Microbubble populations can also be selected for a smaller size, including a nanometer size to increase bubble resonance. For example, a smaller population can be selected as described in U.S. patent application Ser. No. 11/040,999, U.S. publication number 20060078501, which is incorporated herein by reference.

The number of microbubbles of differing sizes in a population can be determined, for example, using an optical decorrelation method. The diameter of microbubbles making up given population can be determined and the number percentage of microbubbles at different sizes can also be determined. For optical decorrelation methods a Malvin™ Zetasizer™ or similar apparatus may be used.

A plurality of microbubbles can be in a physiologically acceptable composition for administration to the subject. Such physiologically acceptable compositions can comprise buffers, diluents, therapeutic or pharmacologic agents, preservatives and others compositions known in the art. Thus, an administered physiologically acceptable composition can comprise a plurality of microbubbles in combination with one or more additional components. Such additional components, can be selected by one skilled in the art based factors including, but not limited to the type of microbubble used and the desired imaging protocol. Factors related to imaging protocol that can direct selection of a suitable additional component, can include, but are not limited to, administration factors (i.e., for example, location), imaging factors (i.e., for example, duration, delay between administration and imaging, tissue or organ imaged, etc.) and subject factors (i.e., for example, type of subject imaged).

Administration of contrast imaging agents of the present invention can be carried out in various fashions, such as intravascularly, intralymphatically, parenterally, subcutaneously, intramuscularly, intraperitoneally, interstitially, hyperbarically, orally, or intratumorly using a variety of dosage forms. One preferred route of administration is intravascularly. For intravascular use the contrast agent is generally injected intravenously, but may be injected intraarterially as well. The useful dosage to be administered and the mode of administration may vary depending upon the age and weight of the subject, and on the particular imaging application intended. The dosage can be initiated at lower levels and increased until the desired contrast enhancement is achieved.

The contrast agent can be administered in the form of an aqueous suspension such as in water or a saline solution (e.g., phosphate buffered saline). The water can be sterile and the saline solution can be a hypertonic saline solution (e.g., about 0.3 to about 0.5% NaCl), although, if desired, the saline solution may be isotonic. The solution also may be buffered, if desired, to provide a pH range of pH 6.8 to pH 7.4. In addition, dextrose may be included in the media.

Exemplary dosing can be based on the body weight of the subject and on composition administered. Generally, however, the dosage can vary with the imaging protocol and the desired imaging characteristics, and can be determined by one skilled in the art. The dosage can be adjusted by the individual researcher. It is further contemplated that the dosage can vary, and can be administered in one or more dose administrations daily, for one or several days.

The contrast agent provided herein, while not limited to a particular use, can be administered intravenously to a laboratory animal. The contrast agent can administered intravenously to a mouse, rat or rabbit. The contrast agent can also be administered to a human patient.

If a small animal subject is used it can be positioned on a heated platform with access to anesthetic equipment. Thus, the methods can be used with platforms and apparatus used in imaging small animals including "rail guide" type platforms with maneuverable probe holder apparatuses. For example, the described systems can be used with multi-rail imaging systems, and with small animal mount assemblies as described in U.S. patent application Ser. No. 10/683,168, now U.S. Pat. No. 7,133,713, entitled "Integrated Multi-Rail Imaging System," U.S. patent application Ser. No. 10/053,748, U.S. publication No. 20050215878, entitled "Integrated Multi-Rail Imaging System," U.S. patent application Ser. No. 10/683,870, now U.S. Pat. No. 6,851,392, issued Feb. 8, 2005, entitled "Small Animal Mount Assembly," and U.S. patent application Ser. No. 11/053,653, entitled "Small Animal Mount Assembly," which are incorporated herein by reference.

Small animals can be anesthetized during imaging and vital physiological parameters such as heart rate and temperature can be monitored. Thus, the system can include means for acquiring ECG and temperature signals for processing and display. The system can also display physiological waveforms such as an ECG, respiration or blood pressure waveform. If a small animal is used, contrast agent can be optionally injected either through the tail vein, through the jugular in a cannulation procedure or directly into the heart.

Also provided is the use of a system for producing an ultrasound image using line-based image reconstruction with the contrast agents and the methods provided herein. One example of such a system may have the following components as described in U.S. patent application Ser. No. 10/736,232, U.S. patent application publication 20040236219, now U.S. Pat. No. 7,052,460, which is set forth in part below and is incorporated herein by reference. The system for producing an ultrasound image using line based image reconstruction can provide an ultrasound image having an effective frame rate in excess of 200 frames per second. The system incorporates an ECG based technique that enables significantly higher time resolution than what was previously available, thus allowing the accurate depiction of a rapidly moving structure, such as a heart, in a small animal, such as a mouse, rat, rabbit, or other small animal, using ultrasound (and ultrasound biomicroscopy).

The intravenous injection can be administered as a single bolus dose, or by repeated injection or continuous infusion. Effective dosages and schedules for administering a given contrast agent can be determined empirically, and making such determinations is within the ordinary skill in the art. The dosage range for the administration of the contrast agents are those large enough to produce the desired ultrasound imaging effect. Such an effect typically includes an increased return from the contrast agent. Such an increased return or intensity of signal from a contrast agent can be indicated by increased brightness on an ultrasound image, which can be represented by coloration of an ultrasound image.

A microbubble contrast agent can be disrupted or destroyed by a pulse of ultrasound. The pulse of ultrasound can be produced by the same or a different transducer as the transducer producing the imaging frequency ultrasound. Therefore, the methods contemplate using a plurality of ultrasound probes and frequencies. The microbubbles can be disrupted or popped by the ultrasound energy at a frequency above or below 20 MHz. As used throughout, "disrupted" or "destroyed" means that a microbubble is fragmented, ruptured, or cracked such that gas escapes from the micro bubble. The micro bubble contrast agent can also be disrupted or destroyed via other means such as chemical interactions with other administered drugs or by altering the oxygenation level of the blood. In some cases this may result in gas diffusion from the bubble. Contrast agent expulsion from the subject can also occur and includes being filtered by the liver and or kidneys or via the contrast agent breaking down or binding with other molecules and organelles already present in the subject including cells, oxygen, and carbon dioxide. Herein the destruction of micro bubbles and other contrast agents will includes both physical destruction methods, such as ultrasound pulses, and chemical destruction methods and expulsion from the subject via other methods and combinations thereof.

The ultrasound or other imaging modality used can be transmitted immediately after administration of contrast agent or at any time interval subsequent to contrast agent administration. Imaging can also begin prior to administration, continue throughout the administration process, and continue subsequent to the completion of administration. The imaging can also take place at any discrete time prior to, during or after administration of the contrast agent.

Any portion of a subject can be imaged. For example, the organ can be selected from the group consisting of a heart, a brain, a kidney, and a muscle. One non-limiting example of an organ that can be imaged is a heart. A non-limiting example of a muscle type that can be imaged is a skeletal muscle. For example, muscles of the limbs can be imaged. As would be clear to one skilled in the art, however, other muscle types can also be imaged, including smooth muscle, and cardiac muscle, such as when the heart is imaged. Other organs that can be imaged include, but are not limited to a lung, a brain, a liver and blood and blood vessels. The organs imaged or portions thereof can be that of a mouse, rat, or other small animal. The systems and methods can also be used to image physiological or pathological processes such as angiogenesis or inflammation.

Other subjects and portions of subjects can also be imaged including individual cells or collections of cells either in vivo or ex vivo as might be grown or collected into a Petri dish. In this case the imaging modality can optionally be optical imaging either with or without a magnifying lens and the contrast agent might be a fluorescent dye which could be used to identify particular parts of the cells, or individual cells expressing a particular genetic marker.

Contrast agents can be targeted or non-targeted or lodging. Several strategies can be used to direct ultrasound contrast agent to a desired target including lodging of bubbles in tissues of the subject based on size.

In regard to microbubble contrast agents, one exemplary targeting strategy takes advantage of the inherent chemical properties of the microbubble shell components. For example, albumin or lipid microbubbles can attach to the surface of target cells via cell receptors.

Contrast agents can also be targeted by conjugation of specific ligands or antibodies that bind to desired markers. A further strategy takes advantage of the physical size of the contrast agent. For example, in regard to microbubbles, bubbles of a certain size can lodge in the microvasculature of a subject, wherein they can be imaged. Lodging can be further augmented by alteration of the microbubble shell charge in order to further enhance the percentage of microbubbles lodging within the microcirculation.

A contrast agent can advantageously be employed as delivery agents for bioactive moieties such as therapeutic drugs (i.e., agents having a beneficial effect on a specific disease in a living human or non-human animal). Thus, for example, therapeutic compounds can be located in a microbubble, may be linked to part of an encapsulating wall or matrix, e.g., through covalent or ionic bonds, if desired through a spacer arm, or may be physically mixed into such encapsulating or matrix material. To deliver an agent a microbubble can be disrupted as described herein. For example, when microbubbles are disrupted or destroyed, drugs or genes that are housed within them or bound to their shells can be released to the blood stream are then delivered to tissue by convective forces through the permeabilized microvessels. Moreover, if the agent is linked or otherwise attached to the microbubble, the agent can be delivered without disrupting the microbubble. For example, a lodged microbubble can deliver a therapeutic agent linked to its shell without being disrupted.

A targeted contrast agents used in the methods described can be targeted to a variety of cells, cell types, antigens, cellular membrane proteins, organs, markers, tumor markers, angiogenesis markers, blood vessels, thrombus, fibrin, and infective agents. For example, targeted microbubbles can be produced that localize to targets expressed in a subject. Desired targets are generally based on, but not limited to, the molecular signature of various pathologies, organs and/or cells. For example, adhesion molecules such as integrin $\alpha_v\beta_3$, intercellular adhesion molecule-1 (I-CAM-1), fibrinogen receptor GPIIb/IIIa and VEGF receptors are expressed in regions of angiogenesis, inflammation or thrombus. These molecular signatures can be used to localize high frequency ultrasound contrast agents through the use of targeting molecules, including but not limited to, complementary receptor ligands, targeting ligands, proteins, and fragments thereof. Target cell types include, but are not limited to, endothelial cells, neoplastic cells and blood cells. The methods described herein optionally use microbubbles targeted to VEGFR2, I-CAM-1, $\alpha_v\beta_3$ integrin, $\alpha_v$ integrin, fibrinogen receptor GPIIb/IIIa, P-selectin, mucosal vascular adressin cell adhesion molecule-1. Moreover, using methods known in the art, complementary receptor ligands, such as monoclonal antibodies, can be readily produced to target other markers in a subject. For example, antibodies can be produced to bind to tumor marker proteins, organ or cell type specific markers, or infective agent markers. Thus, the targeted contrast agents can be targeted, using antibodies, proteins, fragments thereof, or other ligands, as described herein, to sites of neoplasia, angiogenesis, thrombus, inflammation, infection, as well as to diseased or normal organs or tissues including but not limited to blood, heart, brain, blood vessel, kidney, muscle, lung and liver. Optionally, the targeted markers are proteins and may be extracellular or transmembrane proteins. The targeted markers, including tumor markers, can be the extracellular domain of a protein. The antibodies or fragments thereof designed to target these marker proteins can bind to any portion of the protein. Optionally, the antibodies can bind to the extracellular portion of a protein, for example, a cellular transmembrane protein. Antibodies, proteins, or fragments thereof can be made that specifically or selectively target a desired target molecule using methods known in the art.

Such selective or specific binding can be readily determined using the methods and devices described herein. For example, selective or specific binding can be determined in vivo or in vitro by administering a targeted contrast agent and detecting an increase ultrasound scattering from the contrast agent bound to a desired target. Thus a targeted contrast agent can be compared to a control contrast agent having all the components of the targeted contrast agent except a targeting ligand. By detecting increased resonance or scattering from the targeted contrast agent versus a control contrast agent, the specificity or selectivity of binding can be determined. If an antibody or similar targeting mechanism is used, selective or specific binding to a target can be determined based on standard antigen/epitope/antibody complementary binding relationships. Further, other controls can be used. For example, the specific or selective targeting of the microbubbles can be determined by exposing targeted microbubbles to a control tissue, which includes all the components of the test tissue except for the desired target ligand or epitope. To compare a control sample to a test sample, levels of non-linear resonance can be detected by enhanced ultrasound imaging.

Illustrative targeting mechanisms that can be targeted to particular targets and indicated areas of use for targetable diagnostic and/or therapeutic agents include, but are not limited to, antibodies to: CD34, ICAM-1, ICAM-2, ICAM-3, E-selectin, P-selectin, PECAM, CD18 Integrins, VLA-1, VLA-2, VLA-3, VLA-4, VLA-5, VLA-6, GlyCAM, MAd-CAM-1, fibrin, and myosin. These and other targeting molecule molecules are identified and discussed in U.S. Pat. No. 6,264,917, which is incorporated by reference herein generally and specifically for purposes of identifying useful targeting molecule molecules.

Specific or selective targeted contrast agents can be produced by methods known in the art, for example, using the methods described.

For example, targeted microbubble contrast agents can be prepared as perfluorocarbon or other gas-filled microbubbles with a monoclonal antibody on the shell as a ligand for binding to target ligand in a subject as described in Villanueva et al., "Microbubbles Targeted to Intracellular Adhesion Molecule-1 Bind to Activated Coronary Artery Endothelial Cells," *Circulation* (1998) 98: 1-5. For example, perfluorobutane can be dispersed by sonication in an aqueous medium containing phosphatidylcholine, a surfactant, and a phospholipid derivative containing a carboxyl group. The perfluorobutane is encapsulated during sonication by a lipid shell. The carboxylic groups are exposed to an aqueous environment and used for covalent attachment of antibodies to the microbubbles by the following steps. First, unbound lipid dispersed in the aqueous phase is separated from the gas-filled microbubbles by floatation. Second, carboxylic groups on the microbubble shell are activated with 1-ethyl-3-(3-dimethylaminopropyl)carbodimide, and antibody is then covalently attached via its primary amino groups with the formation of amide bonds.

Targeted microbubbles can also be prepared with a biotinylated shell as described in Weller et al., "Modulating Targeted Adhesion of an Ultrasound Contrast Agent to Dysfunctional Endothelium," *Ann. Biomed. Engineering*, (2002) 30: 1012-1019. For example, lipid-based perfluorocarbon-filled microbubbles can be prepared with monoclonal antibody on the shell using avidin-biotin bridging chemistry using the following protocol. Perfluorobutane is dispersed by sonication in aqueous saline containing phosphatidyl choline, polyethylene glycol (PEG) stearate, and a biotinylated derivative of phosphatidylethanolamine as described in the art. The sonication results in the formation of perfluorobutane microbubbles coated with a lipid monolayer shell and carrying the biotin label. Antibody conjugation to the shell is achieved via avidin-biotin bridging chemistry. Samples of biotinylated microbubbles are washed in phosphate-buffered saline (PBS) by centrifugation to remove the lipid not incorporated in the microbubble shell. Next, the microbubbles are incubated in a solution (0.1-10 µg/mL) of streptavidin of in PBS. Excess streptavidin is removed by washing with PBS. The microbubbles are then incubated in a solution of biotinylated monoclonal antibody in PBS and washed again. The resultant microbubble have antibody conjugated to the lipid shell via biotin-streptavidin-biotin linkage. In another example, for targeted microbubbles, biotinylated microbubbles can be prepared by sonication of an aqueous dispersion of decafluorobutane gas, distearoylphodphatidylcholine, polyethyleneglycol-(PEG-) state, and distearoylphosphatidylethanolamine-PEG-biotin.

Microbubbles can then be combined with streptavidin, washed, and combined with biotinylated echistatin.

Targeted microbubbles can also be prepared with an avidinated shell, as is known in the art. In a preferred embodiment, a polymer microbubble can be prepared with an avidinated or streptavidinated shell. For example, a polymer contrast agent comprising a functionalized polyalkylcyanoacrylate can be used as described in patent application PCT/EP01/02802. Streptavidin can be bonded to the contrast agent via the functional groups of the functionalized polyalkylcyanoacrylate. In a preferred embodiment, avidinated microbubbles can be used in the methods disclosed herein. When using avidinated microbubbles, a biotinylated antibody or fragment thereof or another biotinylated targeting molecule or fragments thereof can be administered to a subject. For example, a biotinylated targeting ligand such as an antibody, protein or other bioconjugate can be used. Thus, a biotinylated antibody, targeting ligand or molecule, or fragment thereof can bind to a desired target within a subject. Once bound to the desired target, the contrast agent with an avidinated shell can bind to the biotinylated antibody, targeting molecule, or fragment thereof. When bound in this way, high frequency ultrasound energy can be transmitted to the bound contrast agent, which can produce non-linear scattering of the transmitted ultrasound energy. An avidinated contrast agent can also be bound to a biotinylated antibody, targeting ligand or molecule, or fragment thereof prior to administration to the subject.

When using a targeted microbubble contrast agent with a biotinylated shell or an avidinated shell a targeting ligand or molecule can be administered to the subject. For example, a biotinylated targeting ligand such as an antibody, protein or other bioconjugate, can be administered to a subject and allowed to accumulate at a target site. A fragment of the targeting ligand or molecule can also be used.

When a targeted contrast agent with a biotinylated shell is used, an avidin linker molecule, which attaches to the biotinylated targeting ligand can be administered to the subject. Then, a targeted contrast agent with a biotinylated shell is administered to the subject. The targeted contrast agent binds to the avidin linker molecule, which is bound to the biotinylated targeting ligand, which is itself bound to the desired target. In this way a three step method can be used to target contrast agents to a desired target. The intermediate targeting ligand can bind to all of the desired targets detailed above as would be clear to one skilled in the art.

Targeted contrast agents or non-targeted contrast agents or microbubbles can also comprise a variety of markers, detectable moieties, or labels. Thus, a microbubble contrast agent equipped with or without a targeting ligand or antibody incorporated into the shell of the microbubble can also include another detectable moiety or label. As used herein, the term "detectable moiety" is intended to mean any suitable label, including, but not limited to, enzymes, fluorophores, biotin, chromophores, radioisotopes, colored particles, electrochemical, chemical-modifying or chemiluminescent moieties. Common fluorescent moieties include: fluorescein, cyanine dyes, coumarins, phycoerythrin, phycobiliproteins, dansyl chloride, Texas Red, and lanthanide complexes. Of course, the derivatives of these compounds which are known to those skilled in the art also are included as common fluorescent moieties.

The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable can be employed. The detectable moiety may be inherent to the molecular probe. For example, the constant region of an antibody can serve as an indirect detectable moiety to which a second antibody having a direct detectable moiety can specifically bind.

Other image modalities, as set forth herein, can be used to create reference and data sets. Before and after events or other changes captured by imaging can distinguish between the reference set and the data set. The infusion of contrast agents can be such a "before and after event" whereby the reference set can be acquired using ultrasound imaging prior to the infusion of the contrast agent and the data set can be acquired after the infusion of the contrast agent. Optionally, changes captured by imaging which can determine the timing of a reference set acquisition or a data set acquisition can be any change which can be captured by an imaging modality, such as by non-limiting example a change in thermal characteristics, a change in radar reflectivity, a change in blood flow, a change in magnetic resonance, a change in fluid flow, a change in fluorescence, a change in intensity of visible and non-visible spectra, and a change in proton density, proton spin state, tissue density, tissue elasticity, and attenuation of tissue to X-Rays.

The identified set of reference images and the identified set of data images can be compared. One or more reference images can be compared to a plurality of images of the data image set.

The comparison step of the methods provided for herein can comprise summing the absolute difference of pixel intensity levels and paring the reference set image frame with the data set image frame which yields the smallest absolute difference value. Other methods to compare images can also be used.

The image processing step can comprise the application of a median filter to the image. In one exemplary aspect, the median filter can comprise a 3 by 3 median filter. The image processing step can comprise the application of a blurring filter to the image. In one aspect, the blur filter can comprise a 5 by 5 box filter. In another aspect, the blur filter can comprise a Gaussian filter. The image processing step can comprise the application of image decimation to the image. The image decimation can comprise the use of four adjacent pixels to create one representative pixel. The image decimation can comprise the use of the maximum intensity value of four adjacent pixels as the intensity value of one representative pixel.

Further provided herein is a method for blending the contrast overlay, calculated from a post-event image with respect to a pre-event image, with its corresponding post-event source image.

Also provided herein is a method of creating a persisted overlay frame comprising the steps described above for creating a contrast overlay wherein the persisted overlay frame is created from a moving average of two or more adjacent overlay frames. Persistence can be applied either as a post-processing step, after all images have been acquired, or as an real time acquisition step.

Still further provided herein is a method of creating ultrasound images comprising the steps of acquiring a set of ultrasound reference images of a subject; interposing into the subject contrast agent; acquiring a set of ultrasound data images of the subject; comparing a data set image to each of several reference set images wherein each data set image is associated with the reference set image or images which most closely resembles the data set image; performing image processing on each image of the associated collection; performing image comparison between reference and data set images; performing image subtraction of the two processed images or collection of images wherein a contrast overlay image is created. In the case where one data set image is to be associated with more than one reference set images, the resulting contrast overlays can be combined into a single overlay using averaging, as one non limiting example.

Also provided herein is a method to use an optionally acquired ECG signal to improve the association between data set images and reference set images. For imaging a subject or portions thereof where the subject motion is predominantly cardiac the ECG signal can be used to improve the matching of reference set to data set images. For example, if each reference set image is tagged with a temporal quantifier describing which portion of the heart cycle the image was acquired in, and each data set image that is similarly tagged, the temporal information can be used to restrict the number of reference set images each data set image is compared with. For example, a data set image would only be compared with reference set images which were acquired during the same portion of the heart cycle as the data set image. In this way, the comparison images are known a priori to represent the anatomy in similar positions and state. Reducing the set of comparison images to those that are known to be most similar reduces false positives and also increases processing speed and efficiency. Similar temporal tagging can also be done using other physiological parameters, or biodynamic cycles, such as the respiration signal, blood pressure, temperature, or blood oxygen level.

One non limiting example of the method is shown in FIG. 1. FIG. 1 is a flow diagram in block form showing an exemplary embodiment of the invention. The method 100 is a process which can be performed in a computer or other electronic processing device as described more fully herein. Images can be acquired using methods generally known to one of ordinary skill in the art. These images are commonly stored in frames of a digital format which are arranged in two dimensions with each individual two dimensional point of the frame called a pixel. Multiple frames can be combined in a sequential in time loop to form a movie or as is commonly called in imaging systems, a cine clip.

These images can be acquired using a wide rang of modalities including but not limited to diagnostic ultrasound, x-ray fluoroscopy, MRI, optical imaging, and any other modality capable of acquiring a cine loop of images.

In exemplary method 100, a reference set 101 is identified for use in the method. This reference set 101 comprises of individual images 1 . . . n with an example of one image shown as 102. The reference set 101 can be a subset of a longer data set 103. The reference set 101 can be an image set of a "before" event; that is, an image set taken before some change takes place to or within the subject being imaged. The reference set can be a sub-set of a larger set, for example, in the case where during a continuous acquisition contrast agent is administered at some point during the acquisition. In this case the reference set might consist of the images at the beginning of the set before contrast is administered up to the point where contrast is administered. Another example is to select as the reference set images which occur immediately after or before a destruction sequence. Another further example is to select as the reference set at the end of a long set of separate acquisitions when the level of contrast agent has reached a stable state in the subject or region of imaging. The reference set selected can be applied to data images that occur after the images of the reference set were acquired, or before.

A corresponding data set 103 is identified for use in the method. The data set 103 can be acquired using the same imaging modality and methods that were used for acquisition of the reference set 101. Data set 103 can comprise "after" images; that is, images of the same subject of the reference set acquired after some event, such as the interposition of a contrast agent in the subject or the destruction event designed to remove the contrast agent from the subject. The event can include creating an area of increased contrast in the subject. An area of increased contrast can be created by increasing the intensity of the image in an area of the subject or by decreasing the intensity of the image in an area of the subject. The after event can also be the injection of contrast agents in other modalities. For example, in MRI imaging, after the injection of gadolinium, manganese, iron, gadopentetate dimeglumine, gadoteridol, gadoterate meglumine, mangafodipir trisodium, gadodiamide, perfluorocarbons or other MRI specific contrast agent which would be known to one skilled in the art. For optical imaging an exemplary contrast agent can be a fluorescent dye. The event could also be, in MRI imaging, after a temperature change, change to the applied pulse sequence, gradient coil fields, or pulse frequency. The event is not limited to conditions which cause an increase in image intensity but as well, a decrease in image intensity. For CT and X-Ray based imaging modalities, the event can occur after the injection of barium sulfate, gadolinium, iodine, or other contrast agent as would be known to one skilled in the art.

The data set 103 comprises individual image frames 1 . . . m with an example of one image shown as 104. While the number of reference set images can equal the number of data set frames (n=m), they do not have to be equal. The number of reference set images can also be larger or less than the number of data set images.

The reference set 101 and the data set 103 can comprise three-dimensional (3-D) images. The methods described herein are also applicable to imaging in 3D. For example, in an ultrasound modality, using a separate 3D stepper motor (like the VisualSonics Inc 3D Acquisition Motor), or other moving transducer, the imaging transducer can be stepped across the length of an organ of the subject (call this the Y axis). At each point along the Y axis a number of images can be acquired as a reference set. Upon completion of acquisition, there are a number of reference sets acquired at different positions along the length of the organ. The data set images can be acquired in the same way. For example, in the case of the use of contrast agents, after injection of the contrast agent, data sets at each Y axis position can be acquired. Creation of the contrast overlay can be done as described herein and can be done independently for each acquired position. With the use of 3-D images, the Y axis position can be out of phase with the others in terms of respiration and cardiac cycles. In that event, respiration gating can be used to start the acquisition at the beginning of a respiration cycle. In another aspect, 3-D images acquired using two dimensional phased array transducers can also comprise the reference set and data set.

Once the reference set 101 and data set 103 are identified, a comparison step takes place at block 105. This comparison process 105 creates a difference error measurement for each image in the reference set 101 as compared to each image in the data set 103. The difference error is a measure of the similarity of one image to another. The difference error can be computed using a sum of the absolute difference of intensity levels for corresponding pixels on the reference set image 102 and data set image 104 being compared. Every image of the data set can be compared with every image of the reference set. Using ECG and respiratory signals, the number of comparisons can be reduced to include only those images which occur during the same phase of the ECG and respiration cycles. Other difference error calculations can be simple sum of differences, or correlation techniques (sum of pixel to pixel multiplications). Image comparisons can include image shifts (in any direction) or minor non-linear transforms which morph features while keeping the overall image structures consistent.

In block 106 the difference error is used to associate images in the reference set 101 with images in the data set 103. Optionally, a data set image is paired with a reference set image wherein the two images have the smallest difference error as compared to other possible data set image/reference set image combinations. A data set image can also be paired with a reference set image based on similarity of the two images. For example, substantially similar reference set and data set images ca be paired. Thus, an individual data set image 102 is associated with an individual reference set image 104 which optionally gives the smallest difference error (Equation 1).

$$\text{Net Error} = \sum_{i}^{\textit{All Pixels}} (\textit{ReferenceImage}[i] - \textit{DataImage}[i])^2$$

Equation 1: Sum of absolute differences squared

Alternatively, the sum of absolute differences can be used to determine image similarity (Equation 2).

$$\text{Net Error} = \sum_{i}^{All\ Pixels} Abs(ReferenceImage[i] - DataImage[i])$$

Equation 2: Sum of absolute differences

Alternatively, other comparison techniques can be used such as frequency domain methods, convolution methods such as the cross correlation, or pattern matching methods.

Association of multiple reference set images to a data set image can also be done. Multiple image associations can be done with a frame rate of, for example 15 fps, however any frame rate can be used, or with a frame rate whereby there exists enough image redundancy to perform analysis across multiple images. For example, for each data set image there can be more than one reference set image which is a similar match. In this case the two reference images can be combined to reduce noise and spurious uncorrelated changes. The combination can be a simple average, or a maximum filter (take the maximum pixel value from each of the images to create a third) or median filter. The same process can be applied to the data set images. Typically for each data set image the next acquired image (which can be on the order of 10-60 ms delayed from the previous) is similar. These images can also be averaged or a max filter applied to generate a third target image.

The associated images next undergo individual image processing. The associated reference image 107 is image processed 108 and the associated data image 109 is image processed 110. While the images are called "associated" the image processing at this point in the method is done on each individual image. Image processing 108 and 110 can be the same processing techniques. Image processing 108 and 109 can include decimation which is the process of reducing the frame size. Decimation can provide for increased processing efficiency, more efficient memory usage, and removal of local image intensity differences on the pixel resolution scale. Decimation techniques can include taking the average of an intensity for a pixel neighborhood, or the maximum pixel intensity for a pixel neighborhood, as the representative pixel intensity for the decimated frame.

Exemplary image processing 108 and 110 techniques include the application of one or more of noise reduction filters, contrast enhancement filters, blurring filters, low pass filters, high pass filters, and non-linear filters such as median filters or maximum filters. Noise reduction filters can be of a type such as median filters, averaging or mean filters, mode filters, low pass filters, or Monte Carlo filters. Blurring filters can be of a type such as box filters, or Gaussian filters. Contrast enhancement filters can be of a type such as histogram equalization filters. Some imaging modalities suffer from image and hardware noise. Ultrasound images can be inherently noisy due to speckle which is manifested from the tissue structure itself and not by any flaws in hardware or processing. Filters such as those described above can remove this type of noise and other high frequency noise information. Removal of such noise can improve subsequent image subtraction techniques and can be used to emphasize changes due to contrast enhancement only.

Additional image processing techniques can include linear image transformations to bring dominant image structures closer inline. Exemplary examples of linear transformations include resizing, rotations, and shifts. Non-linear image transformations can also be used and include image morphing.

After each associated image 107 and 109 are processed, an image subtraction is performed 111 whereby the processed reference image is subtracted from the processed data image. The image subtraction 111 can be a subtraction of pixel intensities. For the case of ultrasound imaging, the pixel intensities can represent log compressed envelope data. Non-logged, or linear envelope data can also be processed as well as raw RF data. The subtracted image can optionally have its pixel intensity values of less than zero replaced by an intensity value of zero at block 112. Optionally, pixel intensity values that are greater than zero can be replaced by a value of zero. The choice can depend on whether it is expected that the signal intensity should increase or decrease and the result is improved reduction of false positives. For example, when infusing micro bubble contrast agent the expected result is that blood vessels and tissue increase in brightness. However, at the same time tissue located beneath the blood vessels might undergo shadowing due to attenuation of the ultrasound beam through the now contrast enhanced vessels. This reduction of tissue intensity can be suppressed by zeroing out intensity values of less than zero from the subtracted image. The resulting image produced from the image subtraction 111 is called a contrast overlay or enhanced medical image 113.

The contrast overlay or enhanced medical image 113 can be displayed on top of the source (data) set image from which it was derived as a semi transparent, or opaque overlay. In one aspect, the overlay can be a color overlay that can be overlaid on top of a gray scale image. In another aspect, the B-Mode image can be depicted in color and the contrast overlay can be depicted in a distinguishable color. The display can be done in a blending fashion so that the contrast overlay highlights via intensity (brightness) the regions of change.

In a further aspect, the contrast overlay 113 can be processed by applying a predetermined threshold. Here, the intensity of each pixel of the contrast overlay can be compared to the predetermined threshold, and only those pixels within the contrast overlay that exceed the threshold can be displayed. It is contemplated that the threshold value can be a fixed predetermined value, or it can be under user control.

Figure 2:
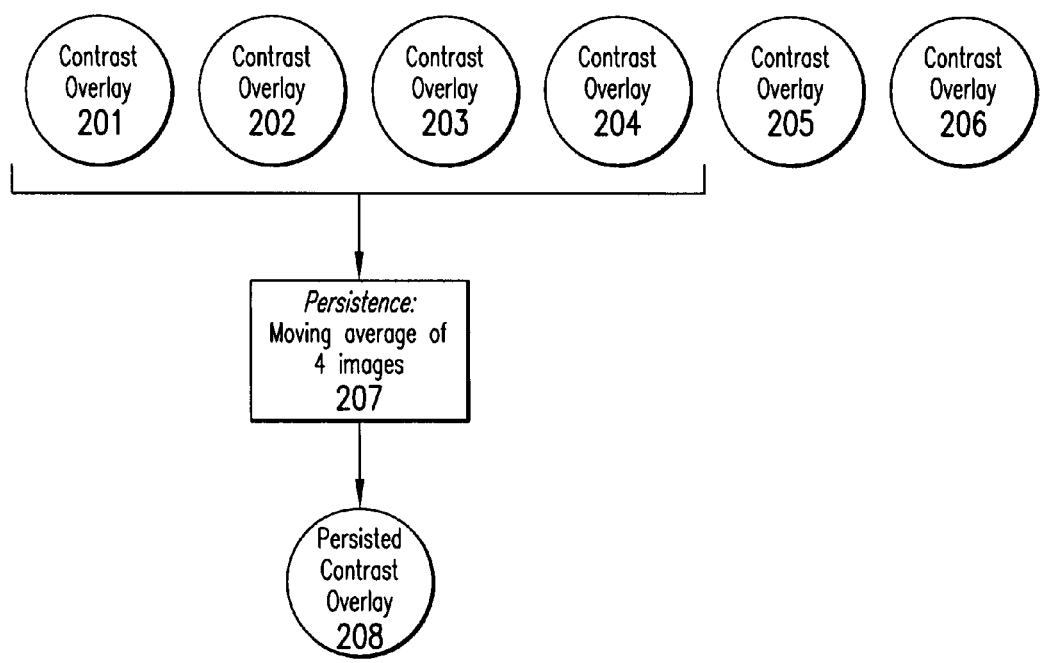
FIG. 2 is a flow diagram in block form showing the creation of a persisted contrast overlay.

Image persistence can also be shown via the steps illustrated in FIG. 2. Two or more contrast overlays can be combined by taking a moving average 207 to create a persisted contrast overlay 208. For example, four contrast overlays, 201, 202, 203, and 204 can be combined as shown in FIG. 2, removing spurious image differences and leaving regions which are similar among the four.

Image persistence can also be performed using a peak hold approach where for each pixel a frame to frame maximum is determined over a moving window of several frames.

Alternatively, frame to frame persistence can be performed using a method comprising the following steps: in the subtracted image (the contrast overlay), evaluate the sign of the difference in pixel level frame to frame; if the sign is positive, meaning the brightness level of that particular pixel has increased compared to the previous frame, set the persistence to zero, i.e., the pixel level in the display frame is equal to the pixel level of the most recent frame; if the sign is negative, meaning that the brightness level of the pixel has decreased, set the persistence to non-zero, so that the pixel level in the display frame decreases exponentially.

Image persistence can also be performed using a maximum intensity projection. In this method, if the intensity of a pixel of a previous frame is larger than the intensity of a pixel in the current frame, the current frames pixel is replaced with the previous pixel value. This has the effect of causing moving reflectors, micro bubbles in blood for example, to cause its path to be traced. An analogous process is keeping the shutter open on a camera while moving a flashlight beam across its field of view. The path of the light beam will be exposed onto the film. The advantage of this type of persistence is to form the ability to map out vessel paths as the micro bubbles progress though the vascular system.

The methods described herein can be implemented in a computer architecture of various types generally known in the art. The several images and information calculated there from can be stored in various forms of data storage generally known in the art including magnetic media or electronic memory.

Aspects of the exemplary systems shown in the Figures and described herein, can be implemented in various forms including hardware, software, and a combination thereof. The hardware implementation can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc. The software comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

Aspects of the exemplary systems can be implemented in computerized systems. Aspects of the exemplary systems can be operational with numerous other general purpose or special purpose computing system environments or configurations. Examples of well known computing systems, environments, and/or configurations that may be suitable for use with the system and method include, but are not limited to, personal computers, server computers, laptop devices, and multiprocessor systems. Additional examples include set top boxes, programmable consumer electronics, network PCs, minicomputers, mainframe computers, distributed computing environments that include any of the above systems or devices, and the like.

Aspects of the exemplary systems can be described in the general context of computer instructions, such as program modules, being executed by a computer. Generally, program modules include routines, programs, objects, components, data structures, etc. that perform particular tasks or implement particular abstract data types. The system and method may also be practiced in distributed computing environments where tasks are performed by remote processing devices that are linked through a communications network. In a distributed computing environment, program modules may be located in both local and remote computer storage media including memory storage devices.

Figure 3:
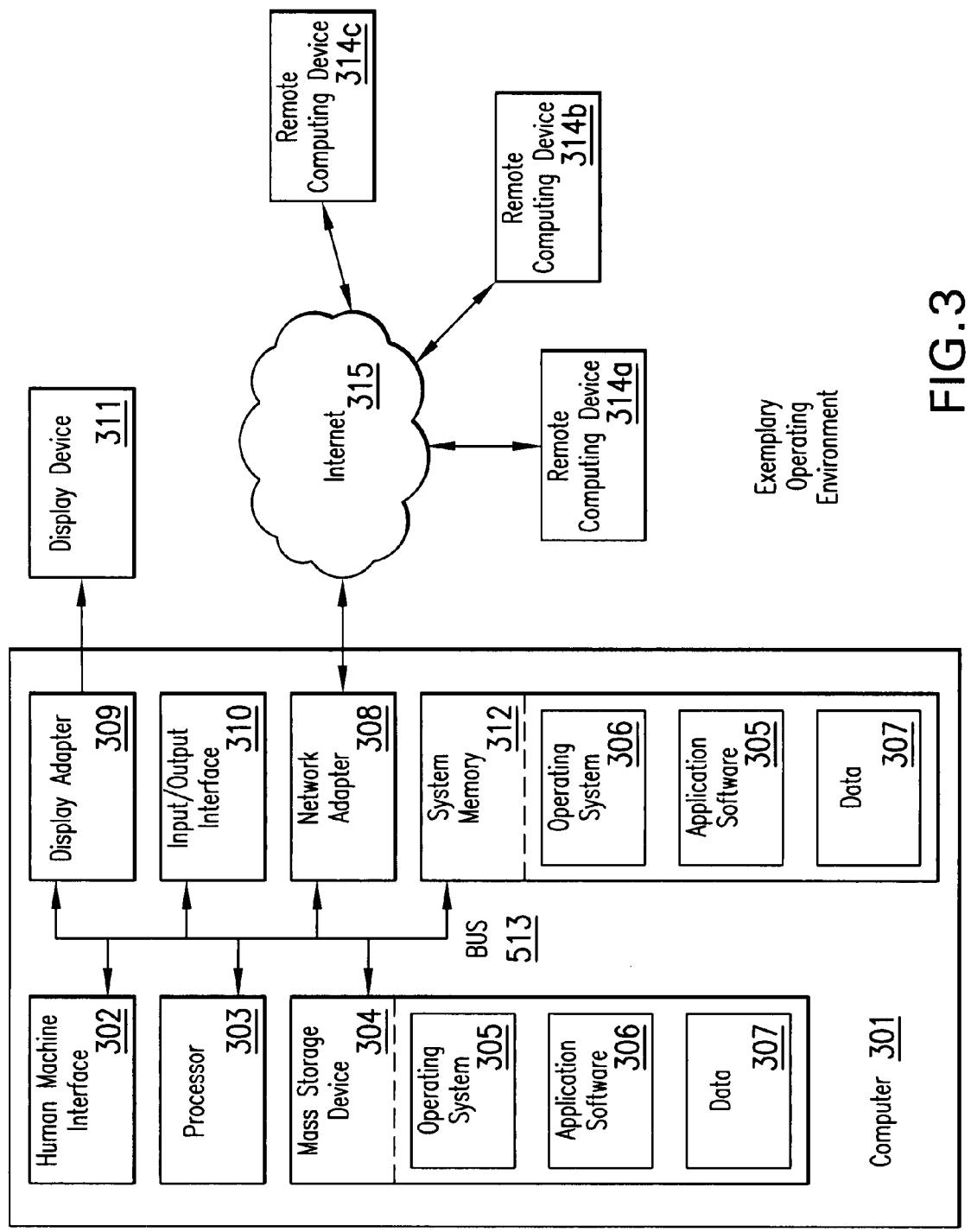
FIG. 3 is a block diagram illustrating an exemplary computing operating environment.

Aspects of the exemplary systems disclosed herein can be implemented via a general-purpose computing device in the form of a computer 301 shown in FIG. 3. The components of the computer 301 can include, but are not limited to, one or more processors or processing units 303, a system memory 312, and a system bus 313 that couples various system components including the processor 303 to the system memory 312.

The system bus 313 represents one or more of several possible types of bus structures, including a memory bus or memory controller, a peripheral bus, an accelerated graphics port, and a processor or local bus using any of a variety of bus architectures. By way of example, such architectures can include an Industry Standard Architecture (ISA) bus, a Micro Channel Architecture (MCA) bus, an Enhanced ISA (EISA) bus, a Video Electronics Standards Association (VESA) local bus, and a Peripheral Component Interconnects (PCI) bus also known as a Mezzanine bus. This bus, and all buses specified in this description can also be implemented over a wired or wireless network connection. The bus 313, and all buses specified in this description can also be implemented over a wired or wireless network connection and each of the subsystems, including the processor 303, a mass storage device 304, an operating system 305, application software 306, data 307, a network adapter 308, system memory 312, an Input/Output Interface 310, a display adapter 309, a display device 311, and a human machine interface 302, can be contained within one or more remote computing devices 314a,b,c at physically separate locations, connected through buses of this form, in effect implementing a fully distributed system.

The computer 301 typically includes a variety of computer readable media. Such media can be any available media that is accessible by the computer 301 and includes both volatile and non-volatile media, removable and non-removable media. The system memory 312 includes computer readable media in the form of volatile memory, such as random access memory (RAM), and/or non-volatile memory, such as read only memory (ROM). The system memory 312 typically contains data such as data 307 and/or program modules such as operating system 305 and application software 306 that are immediately accessible to and/or are presently operated on by the processing unit 303.

Figure 5:
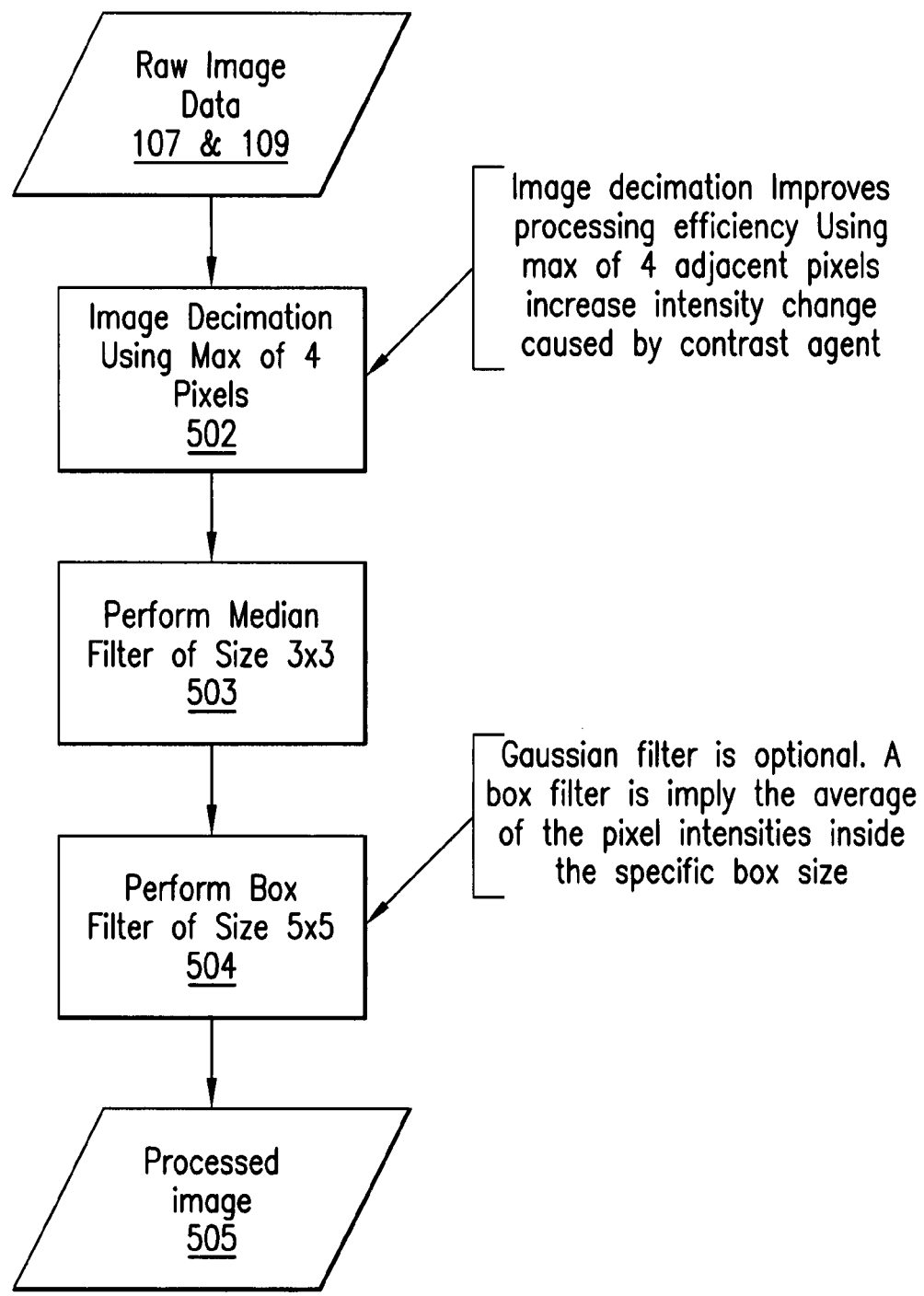
FIG. 5 is a flow diagram of an exemplary image processing block 108 and 110 of FIG. 1.
Figure 6A:
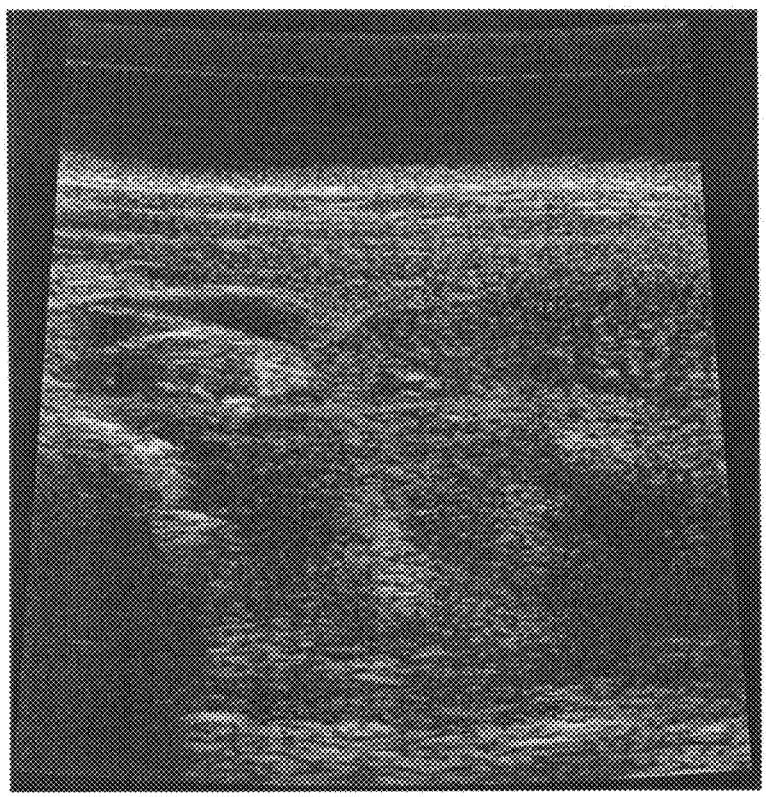
FIG. 6A shows a pre-contrast agent injection reference loop ultrasound image.
Figure 6B:
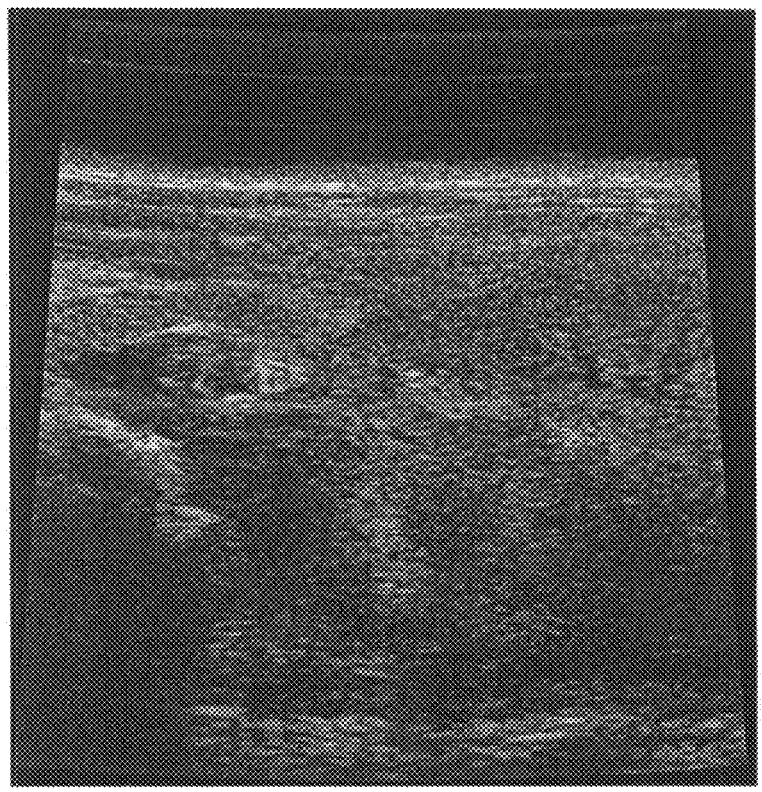
FIG. 6B shows a post contrast agent injection data loop ultrasound image.
Figure 6C:
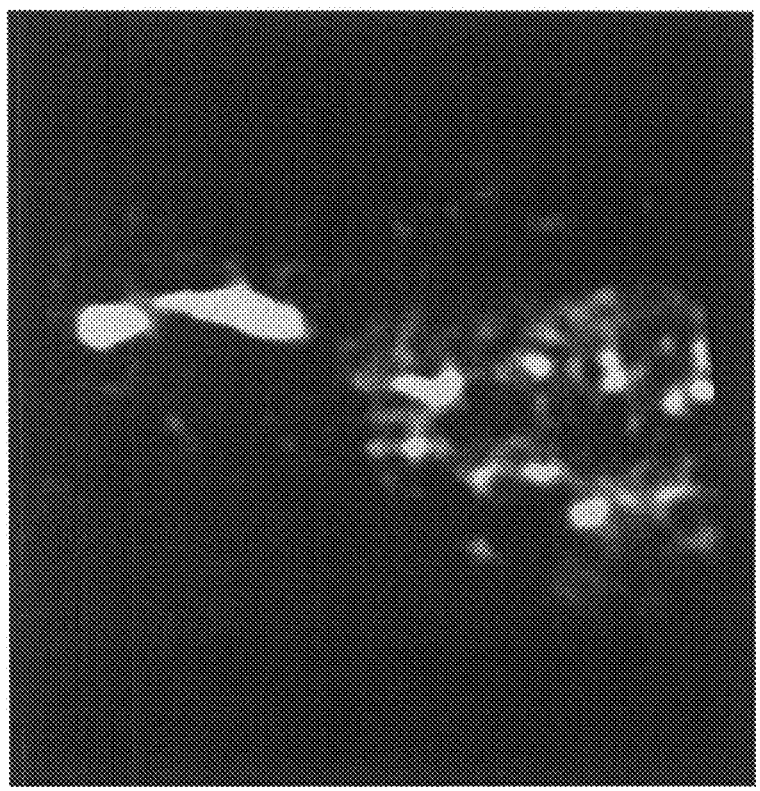
FIG. 6C shows a contrast overlay.
Figure 6D:
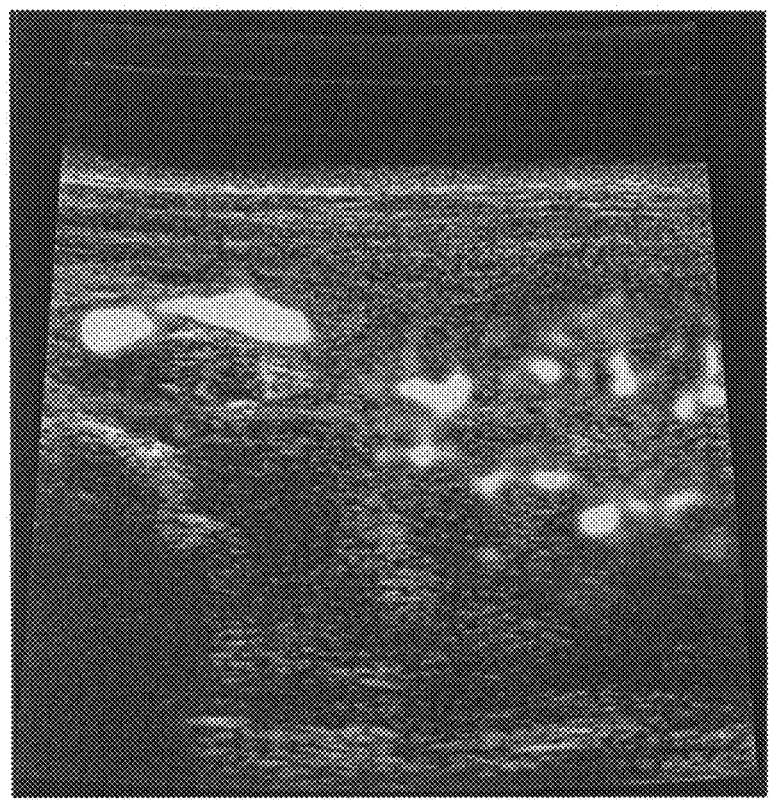
Figure 7A:
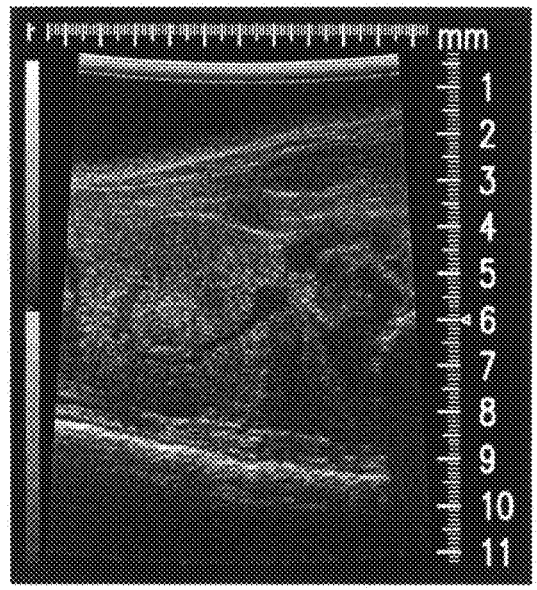
FIGS. 7A and 7B shows results of a bolus injection of microbubbles in healthy kidney at 40 MHz.
Figure 7B:
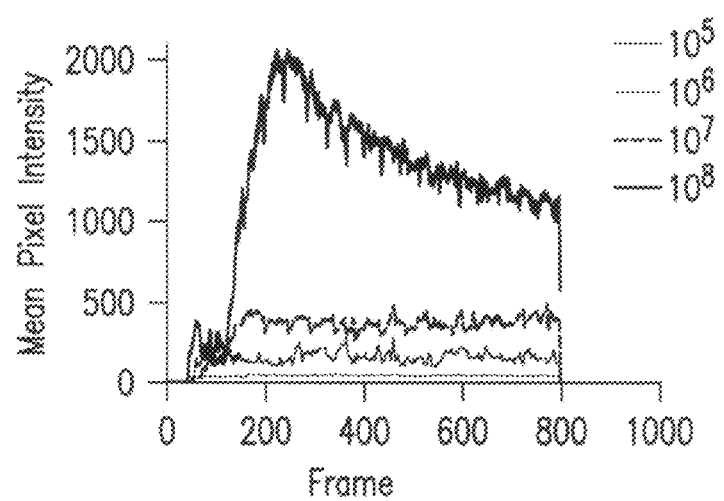
Figure 7C:
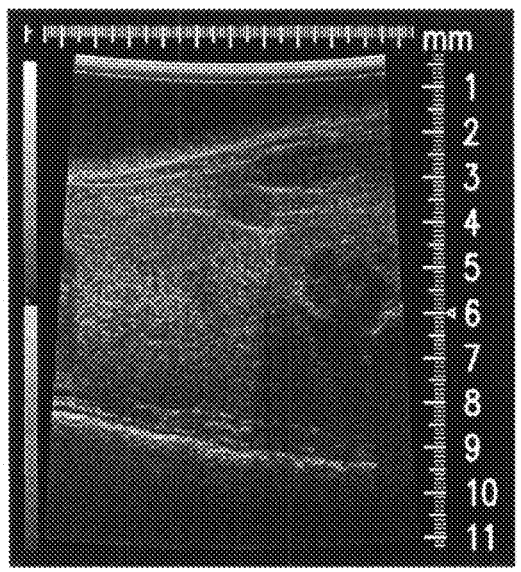
Figure 7D:
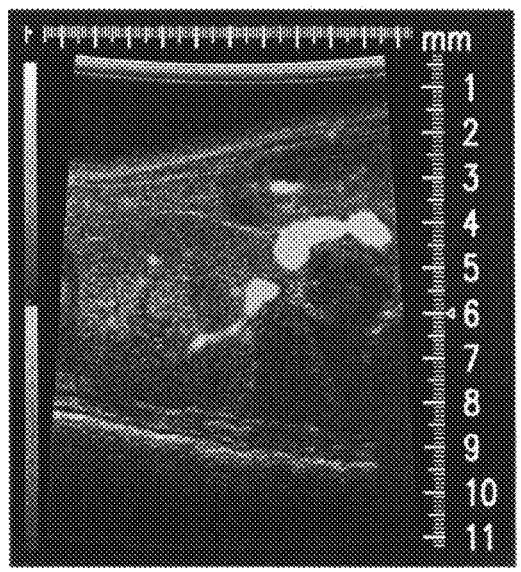
Figure 8A:
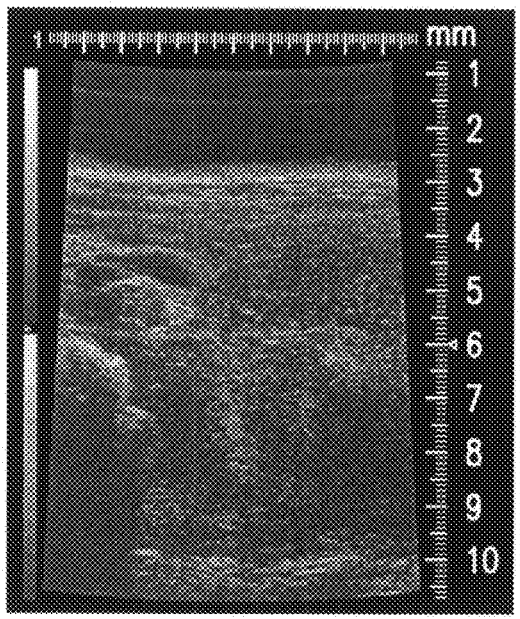
FIG. 8 shows ultrasound images before MB destruction in a kidney. The top row shows post-ischemic in FIG. 8A and healthy contra lateral kidney in FIG. 8B before a destructive pulse. The bottom row shows background-subtracted images of post-ischemic in FIG. 8C and healthy contra lateral kidney FIG. 8D before a destructive pulse.
Figure 8B:
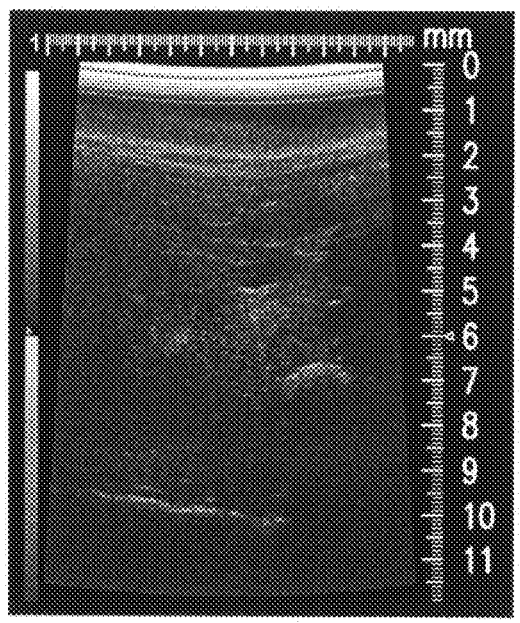
Figure 8C:
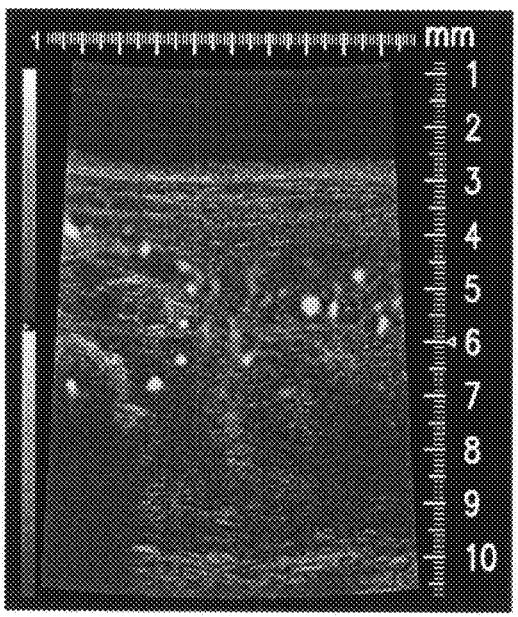
Figure 8D:
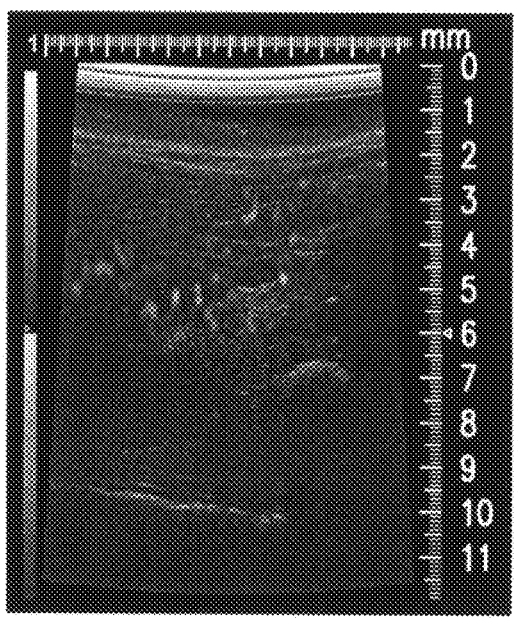

The computer 301 may also include other removable/non-removable, volatile/non-volatile computer storage media. By way of example, FIG. 5 illustrates a mass storage device 304 which can provide non-volatile storage of computer code, computer readable instructions, data structures, program modules, and other data for the computer 301. For example, a mass storage device 304 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Any number of program modules can be stored on the mass storage device 304, including by way of example, an operating system 305 and application software 306. Each of the operating system 305 and application software 306 (or some combination thereof) may include elements of the programming and the application software 306. Data 307 can also be stored on the mass storage device 304. Data 304 can be stored in any of one or more databases known in the art. Examples of such databases include, DB2®, Microsoft® Access, Microsoft® SQL Server, Oracle®, mySQL, PostgreSQL, and the like. The databases can be centralized or distributed across multiple systems.

A user can enter commands and information into the computer 301 via an input device (not shown). Examples of such input devices include, but are not limited to, a keyboard, pointing device (e.g., a "mouse"), a microphone, a joystick, a serial port, a scanner, and the like. These and other input devices can be connected to the processing unit 303 via a human machine interface 302 that is coupled to the system bus 313, but may be connected by other interface and bus structures, such as a parallel port, game port, or a universal serial bus (USB).

A display device 311 can also be connected to the system bus 313 via an interface, such as a display adapter 309. For example, a display device can be a monitor or an LCD (Liquid Crystal Display). In addition to the display device 311, other output peripheral devices can include components such as speakers (not shown) and a printer (not shown) which can be connected to the computer 301 via Input/Output Interface 310.

The computer 301 can operate in a networked environment using logical connections to one or more remote computing devices 314a,b,c. By way of example, a remote computing device can be a personal computer, portable computer, a server, a router, a network computer, a peer device or other common network node, and so on. Logical connections between the computer 301 and a remote computing device 314a,b,c can be made via a local area network (LAN) and a general wide area network (WAN). Such network connections can be through a network adapter 308. A network adapter 308 can be implemented in both wired and wireless environments. Such networking environments are commonplace in offices, enterprise-wide computer networks, intranets, and the Internet 315. The remote computer 314a,b,c may be a server, a router, a peer device or other common network node, and typically includes all or many of the elements already described for the computer 301. In a networked environment, program modules and data may be stored on the remote computer 314a,b,c. The logical connections include a local area network ("LAN") and a wide area network ("WAN"). Other connection methods may be used, and networks may include such things as the "world wide web" or internet.

For purposes of illustration, application programs and other executable program components such as the operating system 305 are illustrated herein as discrete blocks, although it is recognized that such programs and components reside at various times in different storage components of the computing device 301, and are executed by the data processor(s) of the computer. An implementation of application software 306 may be stored on or transmitted across some form of computer readable media. Computer readable media can be any available media that can be accessed by a computer. By way of example, and not limitation, computer readable media may comprise "computer storage media" and "communications media." Computer storage media" include volatile and non-volatile, removable and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer. An implementation of the disclosed method may be stored on or transmitted across some form of computer readable media.

The processing of the disclosed method can be performed by software components. The disclosed method may be described in the general context of computer-executable instructions, such as program modules, being executed by one or more computers or other devices. Generally, program modules include computer code, routines, programs, objects, components, data structures, etc. that perform particular tasks or implement particular abstract data types. The disclosed method may also be practiced in grid-based and distributed computing environments where tasks are performed by remote processing devices that are linked through a communications network. In a distributed computing environment, program modules may be located in both local and remote computer storage media including memory storage devices.

Figure 4:
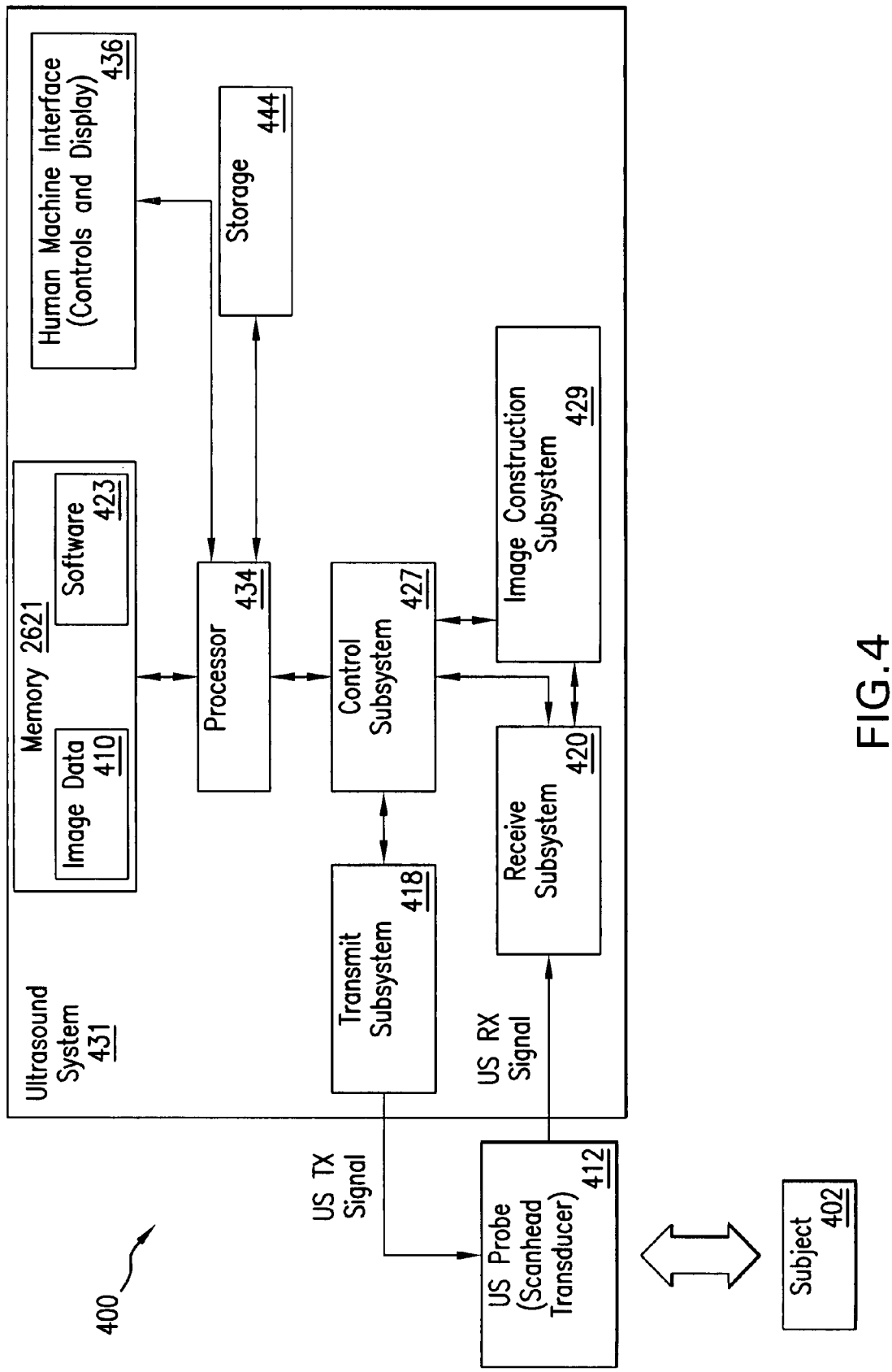
FIG. 4 is a block diagram illustrating an exemplary ultrasound imaging system.

FIG. 4 is a block diagram illustrating an exemplary ultrasound imaging system 400 for creating an image overlay. The ultrasound imaging system is exemplary only. As described throughout, other imaging modalities can also be used. The imaging system 400 operates on a subject 402. An ultrasound probe 412 is placed in proximity to the subject 402 to obtain ultrasound image information. The ultrasound probe 412 can comprise a mechanically moved transducer, or an array that can be used for collection of ultrasound data 410. For example, the transducer can both transmit ultrasound waves to the subject 402 and receive ultrasound waves or backscatter from the subject 402 and can receive a return from contrast agent located in the subject. An ultrasound system 431 can cause the transducer 412 to emit ultrasound by sending a transmitter control signal, USTX signal.

The transducer within the probe 412 can be an array, single element transducer or some other suitable transducer. The transducer can transmit ultrasound at a low frequency, such as frequencies less than or equal to 20 megahertz (MHz). For example, the transducer can transmit ultrasound at or below about 20 MHz, 15 MHz, 10 MHz, 5 MHz, or some other suitable frequency. Further, transducer operating frequencies significantly lower than those mentioned are also contemplated. The transducer can also transmit ultrasound at a high frequency, such as frequencies greater than or equal to 20 megahertz (MHz). For example, the transducer can transmit ultrasound at or above about 20 MHz, 25 MHz, 30 MHz, 35 MHz, 40 MHz, 45 MHz, 50 MHz or some other suitable frequency. Further, transducer operating frequencies significantly higher than those mentioned are also contemplated.

The ultrasound system 431 includes a control subsystem 427, an image construction subsystem 429, a transmit subsystem 418, a receive subsystem 420, and a user input device in the form of a human machine interface 436. A processor 434 is coupled to the control subsystem 427 and the display 416 is coupled to the processor 434.

A memory 421 is coupled to the processor 434. The memory 421 can be any type of computer memory, and is typically referred to as random access memory "RAM," in which the software 423 of the invention executes. Software 423 controls the acquisition, processing and display of the ultrasound data allowing the ultrasound system 431 to display an image. The software also allows for the processing and comparison of images, as described in the disclosed methods.

The method and system for creating an image overlay can be implemented using a combination of hardware and software. The hardware implementation of the system can include any or a combination of the following technologies, which are all well known in the art: discrete electronic components, a discrete logic circuit(s) having logic gates for implementing logic functions upon data signals, an application specific integrated circuit having appropriate logic gates, a programmable gate array(s) (PGA), a field programmable gate array (FPGA), etc.

The software for the system 400 comprises an ordered listing of executable instructions for implementing logical functions, and can be embodied in any computer-readable medium for use by or in connection with an instruction execution system, apparatus, or device, such as a computer-based system, processor-containing system, or other system that can fetch the instructions from the instruction execution system, apparatus, or device and execute the instructions.

In the context of this document, a "computer-readable medium" can be any means that can contain, store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM), a read-only memory (ROM), an erasable programmable read-only memory (EPROM or Flash memory) (magnetic), an optical fiber (optical), and a portable compact disc read-only memory (CDROM) (optical). Note that the computer-readable medium could even be paper or another suitable medium upon which the program is printed, as the program can be electronically captured, via for instance optical scanning of the paper or other medium, then compiled, interpreted or otherwise processed in a suitable manner if necessary, and then stored in a computer memory.

The ultrasound system 431 includes software 423 stored in the memory 421. This software can include system software, as well as, software to process and compare ultrasound backscatter and to formulate images, as described herein, to perform the described methods. The software 423 can also include image or overly comparison software and frame selection software.

Memory 421 also includes the ultrasound data 410 obtained by the ultrasound system 431. A computer readable storage medium 438 is coupled to the processor 434 for providing instructions to the processor 434 to instruct and/or configure the processor 434 to perform algorithms related to the operation of ultrasound system 431. The computer readable medium can include hardware and/or software such as, by the way of example only, magnetic disk, magnetic tape, optically readable medium such as CD ROMs, and semiconductor memory such as PCMCIA cards. In each case, the medium may take the form of a portable item such as a small disk, floppy disk, cassette, or may take the form of a relatively large or immobile item such as a hard disk drive, solid state memory card, or RAM provided in the support system. It should be noted that the above listed example mediums can be used either alone or in combination.

The ultrasound system 431 includes a control subsystem 427 to direct operation of various components of the ultrasound system 431. The control subsystem 427 and related components may be provided as software for instructing a general purpose processor or as specialized electronics in a hardware implementation. The ultrasound system 431 includes an image construction subsystem 429 for converting the electrical signals generated by the received ultrasound echoes (or backscatter) to data that can be manipulated by the processor 434 and that can be rendered into an image or graphical depiction on the display 416. The control subsystem 427 is connected to a transmit subsystem 428 to provide ultrasound transmit signal, USTX signal, to the ultrasound probe 412. The ultrasound probe 412 in turn provides an ultrasound receive signal to a receive subsystem 420. The receive subsystem 420 also provides signals representative of the received signals to the image construction subsystem 429. The receive subsystem 420 is also connected to the control subsystem 427. The image construction subsystem 429 is directed by the control subsystem 427 to operate on the received data to render an image for display using the image data 410.

The receive subsystem 420 is connected to the control subsystem 427 and an image construction subsystem 429. The image construction subsystem 429 is directed by the control subsystem 427. The ultrasound system 431 transmits and receives ultrasound data with the ultrasound probe 412, provides an interface to a user to control the operational parameters of the imaging system 400, and processes data appropriate to formulate still and moving images that represent anatomy and/or physiology. Images are presented to the user through the display 416.

The human machine interface 436 of the ultrasound system 431 takes input from the user and translates such input to control the operation of the ultrasound probe 412. The human machine interface 436 also presents processed images and data to the user through a display. Software 423 in cooperation with the image construction subsystem 429 operate on the electrical signals developed by the receive subsystem 420 to develop an ultrasound image and/or representations and/or comparisons of ultrasound backscatter data received from areas of interest of the subject.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Embodiments of the invention comprise a method for the imaging of contrast agents for high-resolution, high-frequency ultrasound imaging of animal subjects including rodent models.

As described above, contrast agents can flow in the blood stream of the animal and can be deposited at any site that the blood flows. Contrast agents can also be prepared in such a way that they can attach themselves to specific markers in the animal. This "targeted" contrast agent technique uses ligands and antibodies to latch onto specific targets. Contrast agents can also be used for image enhancement to allow a user to easily distinguish small vessels in the organ. In one aspect, perfusion imaging is a way of injecting contrast agent into the animal, allowing the agent to circulate and then the agent can be destroyed using a destruction event. The time taken for the re-perfusion is meaningful to the researcher in quantifying perfusion. This image processing method is not specific to the imaging of targeted or untargeted contrast agents.

Embodiments exploit the brightness change or increase in intensity of an image, to determine how much, and where the contrast agent flows and where it is deposited. The methods described herein can be used with or without ECG or respiration gating.

Contrast agents can be gas filed bubbles with diameters ranging from about 1 to about 4 microns. The bubble size distribution can range form sub-micron size to up to about 10 micron in size. Exemplary contrast agents can be acquired from ImaRx, Targeson, Bracco, or VisualSonics Inc. The ImaRx bubble has an average size of 0.9 microns, the Targeson bubble has a range of 2 to 4 microns in size.

The animal is typically anesthetized and contrast agent can be injected through the tail vein, through the jugular in a cannulation procedure or directly into the heart. The typical image procedure is as follows:

Ultrasound Setup

The ultrasound machine is set up according to the following parameters: position the ultrasound scanhead to image the organ of interest. (In this example, the hind limb and the kidney); set the frame rate to approximately 15 frames per second or optionally, increased frame rates may be used if the total power deposited does not affect the contrast agent itself; and set the power to 50% or such level as not to significantly disturb the contrast agent.

The flow diagram for this process is shown in FIG. 100 and described generally herein.

Reference Loop

The reference loop 101 is a set of n images acquired when contrast agent has not permeated the tissue of interest: either before contrast agent has been injected, after the bubbles have passed through the animal, or after a destruction sequence (bubbles are destroyed in real-time by applying a high power pulse through the transducer. The reference loop 101 can be long enough to encompass 2-3 respiration cycles, and 2-3 cardiac cycles. At a frame rate of 15 frames per second, 30-60 frames are sufficient.

| Sequence of events | | |
|---|---|---|
| Step | Action | Observation |
| 1 | Start capturing a cine clip. | The organ of interest is displayed live on the ultrasound monitor. |
| 2 | Inject a bolus of contrast agent after about 10 seconds of imaging. | The blood vessels turn bright due to the enhancement. The ultrasound image intensity increases wherever contrast agent is present. |
| 3 | Continue image capture for approximately 1 minute and then stop imaging. | The penetration of the agent is observed into the organ of interest. |
| 4 | Save the cine clip. | The ultrasound machines saves approximately 800 frames of data. |
| 5 | Wait for approximately 4 minutes. | The image is frozen on the screen as the agent dissipated through the body and is trapped in the lungs or metabolized in the body. |
| 6 | Start image capture again | The agent is not as concentrated as seen in step 2. Agent is seen in the organ either by lodging in the small capillaries or by binding to the appropriate target for the targeted case. |
| 7 | Initiate a destruction sequence approximately 20 seconds after starting | The destruction sequence distorts the entire image. |
| 8 | Continue imaging | The image has returned to a state as seen before the bolus injection. |
| 9 | Stop imaging and save the cine clip. | |
| 10 | Retrieve the first cine clip saved in step 4. | |
| 11 | Mark the first 40 to 60 frames as the reference cine clip | No contrast agent is observed in the blood vessels. |
| 12 | Process the entire cine clip by using the image processing algorithm described below. | |
| 13 | Play back the processed cine clip. | All contrast agent is displayed as an overlay on the regular B-Mode image. The overlay can be colorized. |
| 14 | Retrieve and process the second cine clip saved in step 9 | Before the destruction phase a much lower amount of contrast is visible. After the destruction sequence only very small traces of agent are visible. |

The method of the exemplary invention uses two sets of images: a reference loop of image frames 101, and a post-injection data loop of image frames 103. The data loop 103 typically refers to a series of sequential frames organized as a cine clip. The position of the animal can be as static as possible to minimize false readings. The processing method also has inherent stability for small changes in image positioning due to things such as respiration and cardiac motion. The reference sets and data sets are then compared with each other to find the associated frames which are more similar 105 and 106. Each image of the associated frames, 107 and 108, is then processed with filters to remove certain local image features 108 and 109. They are then subtracted 111 and a difference map generated which forms the contrast overlay 113. The contrast overlay can be a colorized version of the result that is then overlaid onto the original B-Mode image.

The destruction sequence can comprise a sequence of ultrasound pulses which cause the contrast agent to be destroyed. For micro bubble imaging this involves transmitting ultrasound pulses, either from the imaging transducer itself, or an external second transducer aligned along the plane of imaging or designed to insonate the entire animal. The transmit pulses can cause a high mechanical pressure (sometimes referred to as mechanical index—MI) to the micro bubbles causing them to burst. This can be accomplished by maximizing the transmit power and number of pulses transmitted. The bandwidth of the pulses can be kept high as to incite any frequency dependent resonances across the largest range of bubble sizes.

The reference loop 101 can be a sub-loop of a larger set, captured at the beginning, middle, or end of the loop. The reference loop can comprise a set of images of any size as required by the operator. Its size can be prescribed by the largest amount of images which can be seen to not contain contrast enhancement. Determining which frames based on the presence of contrast is known to a person of ordinary skill in the art. The reference can be a retrospective look at the mouse, after the contrast agent has flushed from the mouse or after a destruction sequence.

The reference loop 101 is a snap shot of the state of the mouse over a small period of time. During this time the animal goes through a number of motion cycles and general image adjustments. These image differences are all captured in the reference loop.

Data Loop

The data loop 103 comprises images outside of the reference loop 101. It can occur before the reference loop 101, after, or include images from the reference loop 101. Typically the reference loop 101 is acquired during a period where there is no contrast agent in the animal. The data loop 103, however, can be acquired as contrast agent is flowing into the tissues. This causes the tissues and vessels to increase in reflectivity and consequently brightness on the image. The data loop 103 can be longer than the reference loop 101 and can account for several minutes' worth of data. Multiple data loops 103 can also exist at different time points after contrast injection or after a destruction sequence.

Reference Loop—Data Loop Association

After identification of the reference loop 101 and the data loop 103 a next step is to associate images from the data loop to their partner image in the reference loop. It is expected that images in the data loop 103 undergo small motion changes. In order to do a final comparison between post and pre contrast agent injections, similar features are compared. Each data loop frame 104 is compared with each reference loop frame 102, using an absolute-sum-of-differences technique 105. Alternatively, other comparison techniques previously described herein can be used. The two images demonstrating the smallest total difference (Equation 3) can be associated. These are the images that are most similar of the two sets.

$$\text{Net Error} = \sum_{i}^{All\ Pixels} (ReferenceImage[i] - DataImage[i])^2$$

Equation 3: Sum of absolute differences

Image Subtraction

Once the associated frames have been determined, the images can be processed 108 and 110 to generate difference maps. A number of image processing algorithms are applied in steps 108 and 109 as shown in FIG. 5.

Images 107 or 109 are first decimated 502 by a factor of 2 in each direction (horizontal and vertical) to increase processing efficiency, memory usage, and to remove local image intensity differences on the pixel-resolution scale. Changes at this scale are evident regardless of the modality or accuracy of the experiment. Image decimation selects the maximum intensity of 4 adjacent pixels as the representative pixel intensity.

A median filter 503 of size 3×3 is then used to further reduce image noise and small resolution changes. An addition box blur 504 filter of size 5×5 smoothes out image features. A Gaussian filter may optionally replace the box filter used here as well. The processed images are then subtracted in block 111. Subtracting these processed images gives a difference map showing the intensity changes.

The reference images 101 represent the non-contrast enhanced images and thus are less bright than the data loop images 103. This information allows for the exclusion of regions of the difference map where the data image is less bright than the reference image 112. The final result is an overlay 113 showing the regions of the image that show increased brightness over the reference loops.

Image persistence can be done as described herein. Also, quantification of data can be done by selecting a region-of-interest from the final processed data set. This can be over the target organ or vessel. From each image the mean intensity of the image difference overlay is determined. This information is plotted as a function of time to give an intensity profile. The shape of this profile gives quantitative information regarding the dynamics, and quantity of contrast markers in the target tissue.

Additionally, the wash out rate of the contrast agent can be observed over a period of time. Once the reference frames have been acquired, and the contrast agent has been injected, a specified number of image frames can be collected at specified time intervals; e.g., 1 second of image data is collected every 10 seconds. This allows for observation of the wash out over a long period of time without an excessive amount of data collected.

In a further aspect, the contrast overlay 113 can be processed by applying a predetermined threshold. Here, the intensity of each pixel of the contrast overlay can be compared to the predetermined threshold, and only those pixels within the contrast overlay that exceed the threshold can be displayed. It is contemplated that the threshold value can be a fixed predetermined value, or it can be under user control.

The contrast overlay 113 is displayed on top of the B-Mode image using a blending algorithm. This method is designed to allow the contrast overlay 113 to be displayed as a semi transparent color map on top of the grayscale B-Mode image. The level of transparency is user controlled.

FIG. 6 shows images created using the exemplary method described herein. FIG. 6A shows a pre-contrast agent injection reference loop ultrasound image. FIG. 6B shows a post contrast agent injection data loop ultrasound image. FIG. 6C shows a contrast overlay. FIG. 6D shows the data loop image of FIG. 6B with the contrast overlay of FIG. 6C blended in. As discussed above, colorization can be used in the methods of the present invention, particularly where colorization can help to visually represent the areas of contrast agent presence.

An exemplary blending algorithm in pseudo-code for an exemplary 8-bit image is:

```
iColour = intensity of Contrast overlay pixel (0 – 255)
iGray = intensity of B-Scan pixel (0 – 255)
iBlendValue = level of transparency (0-255)
iAtemp = iColour – iBlendValue;
if(iAtemp<0)
    iAtemp=0;
iBtemp = 256 – iAtemp;
iTemp = iGray * iBtemp;
NewPixelRed = (OverlayPalette[iColour].Red*iAtemp + iTemp) / 256;
NewPixelBlue = (OverlayPalette [iColour].Green*iAtemp + iTemp) / 256;
    NewPixelGreen = (OverlayPalette [iColour].Blue*iAtemp +
    iTemp) / 256;
```

Example 2

Materials and Methods

Inflammation in the mouse hindleg was induced by a one or three hour treatment with TNF-alpha injected subcutaneously into the hindpaw. Inflammation in the kidney was induced by ischemia-reperfusion injury. The left kidney was exposed and the renal artery was clamped for 32 minutes, followed by 2 hours of re-perfusion as described in Singbartl K, Green S A, Ley K. (2000) "Blocking P-selectin protects from ischemia/reperfusion induced acute renal failure" *FASEB J.* 14: 48-54. The wound was closed in layers and, covered with a saline-soaked gauze.

Targestar$^B$ microbubbles from Targeson (Charlottesville, Va.) were targeted to P-selectin by conjugating an anti-P-selectin monoclonal antibody to the surface of the MB per manufacturer's instructions. The MB were diluted to a concentration of $10^7$ or $10^8$ MB in 100 µL of phosphate-buffered saline, and injected as a bolus through a cannula placed in the left jugular vein.

Ultrasound imaging was performed using a VisualSonics™ (Toronto, Calif.) model VEVO® 770 at 30 or 40 MHz. Cine loops of 800 frames were recorded for all studies. Frame rate was held constant at 17 Hz. The Vevo® system included software for comparing, matching and subtracting data set images and reference set images. For example, Vevo® Contrast Mode software was used. Wash-in of MB through the imaged tissue immediately after injection was recorded, and imaging was suspended for 4 minutes to allow circulating MB to accumulate at the target site. The targeted tissue was then imaged for about 100 frames, and a pulsing sequence to destroy microbubbles in the ultrasound field was applied. The tissue was imaged for several hundred frames after destruction to assess the contrast due to circulating (not adherent) microbubbles.

The first 100 frames following the destruction sequence were selected as a reference set, and represented the contrast signal due to freely-circulating MB. A region of interest (ROI) encompassing the kidney or saphenous vein and medial large muscle was selected. The spatially-averaged pixel intensities of the reference images within the ROI were subtracted from the 100 frames before destruction (data set images) to derive the contrast signal due to adherent microbubbles. Wash-in following MB injection was assessed by setting 100 frames prior to injection as a reference set, and subtracting this from succeeding frames.

Results

FIG. 7 shows results of a bolus injection of microbubbles in healthy kidney at 40 MHz. FIG. 7A shows kidney before injection and 1C shows the kidney after injection. Background-subtracted contrast enhancement after injection (green scale) is shown in FIG. 7D. FIG. 7B shows pixel intensity averaged over a ROI encompassing the kidney for bolus injections of $10^5$, $10^6$, $10^7$, and $10^8$ MB.

FIG. 8 shows ultrasound images before MB destruction in a kidney. The top row shows post-ischemic in FIG. 8A and healthy contra lateral kidney in FIG. 8B before a destructive pulse. The bottom row shows background-subtracted images of post-ischemic in FIG. 8C and healthy contra lateral kidney FIG. 8D before a destructive pulse.

Figures 9A, 9B:
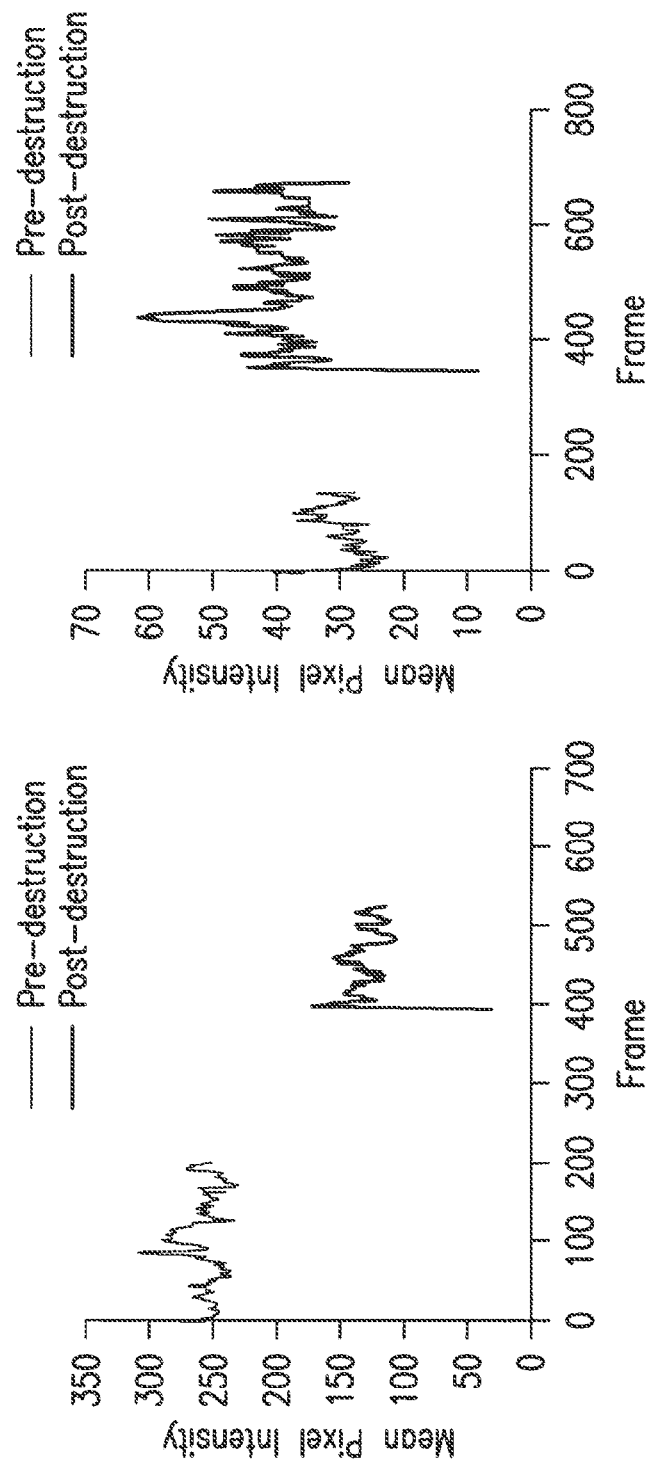
FIG. 9 shows background-subtracted mean pixel intensity of ROI around kidney showing contrast enhancement in a post-ischemic kidney in FIG. 9A and in a healthy contra lateral kidney in FIG. 9B.

FIG. 9 shows background-subtracted mean pixel intensity of ROI around kidney showing contrast enhancement in a post-ischemic kidney in FIG. 9A and in a healthy contralateral kidney in FIG. 9B.

Figure 10:
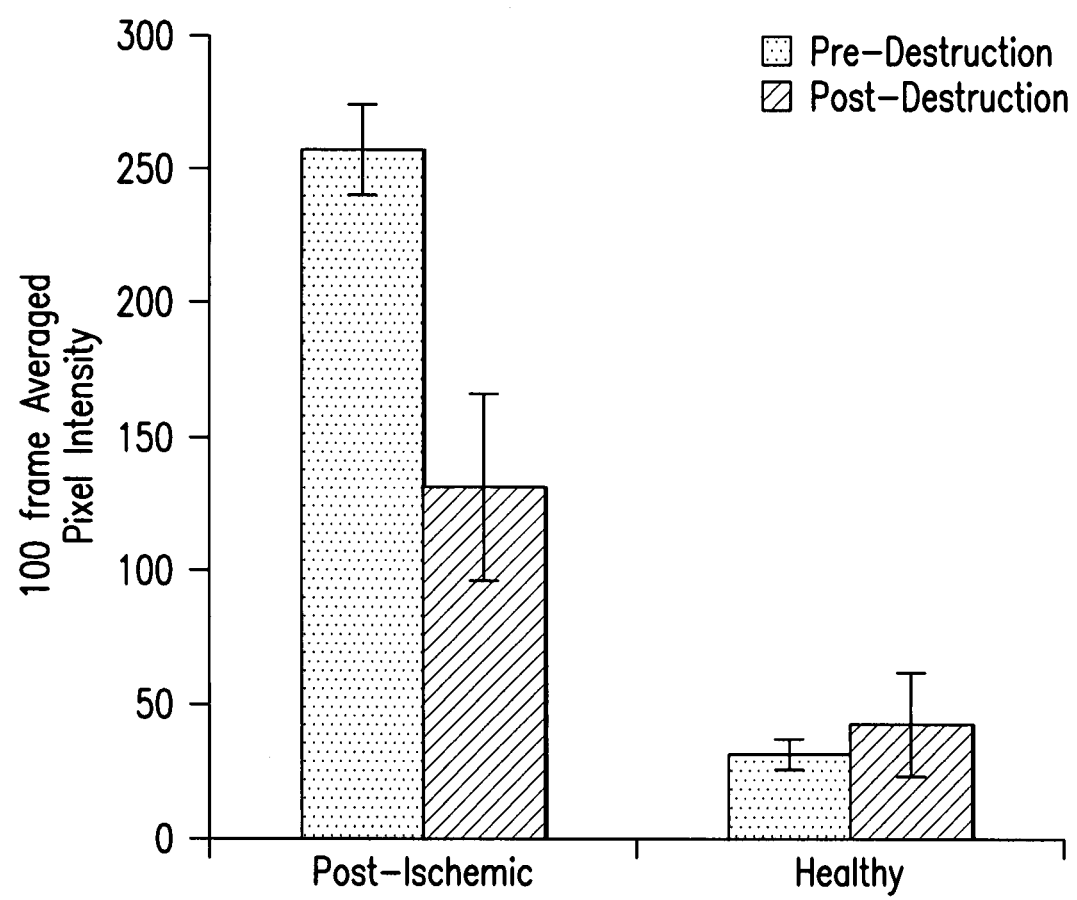
FIG. 10 shows pixel intensity within ROI averaged over 100 frames before a destructive pulse and after MB destruction. Error bars show standard deviation over 100 frames.
Figure 11A:
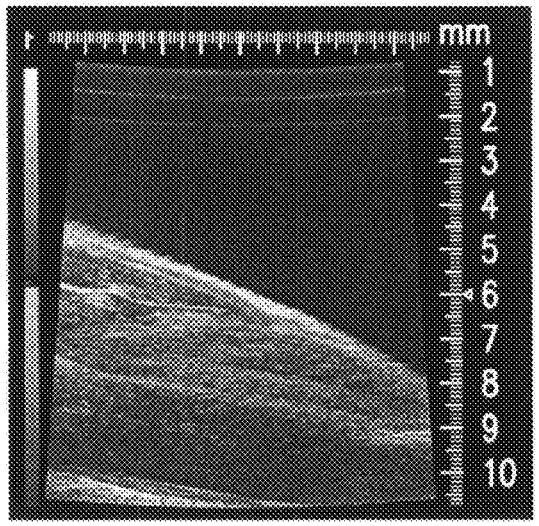
FIG. 11 shows ultrasound images before micro bubble destruction in hind leg. The top row shows 3-hour TNF-alpha treated in FIG. 11A and healthy untreated hind leg in FIG. 11B before a destructive pulse. The bottom row shows background-subtracted images of 3-hour TNF-alpha treated in FIG. 11C and healthy untreated hind leg in FIG. 11D before a destructive pulse.
Figure 11B:
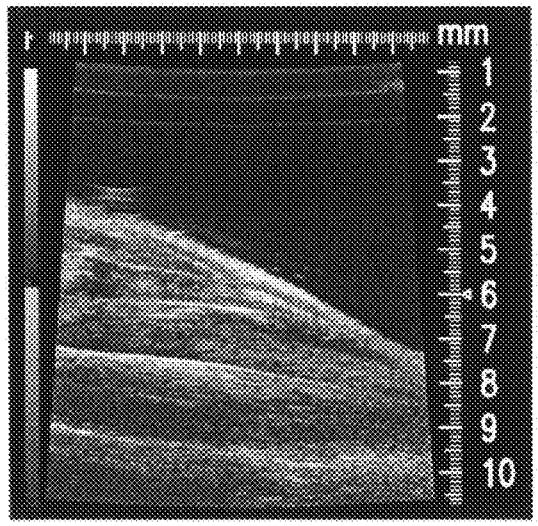
Figure 11C:
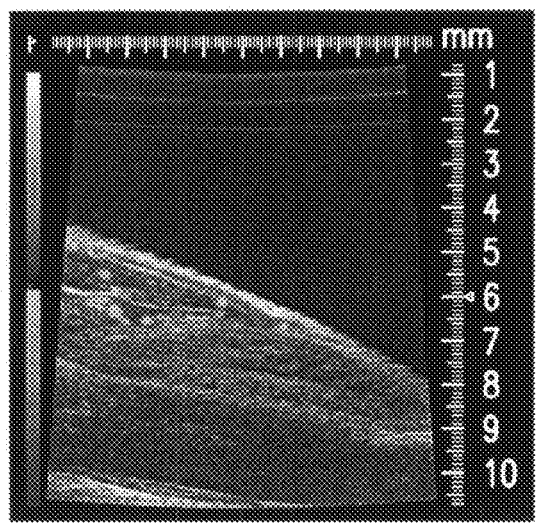
Figure 11D:
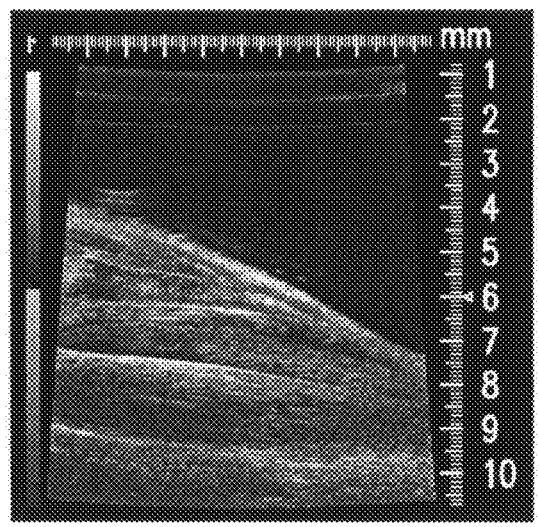

FIG. 10 shows pixel intensity within ROI averaged over 100 frames before a destructive pulse and after MB destruction. The error bars show standard deviation over 100 frames.

FIG. 11 shows ultrasound images before MB destruction in hindleg. The top row shows 3-hour TNF-alpha treated in FIG. 11A and healthy untreated hindleg in FIG. 11B before a destructive pulse. The bottom row shows background-subtracted images of 3-hour TNF-alpha treated in FIG. 11C and healthy untreated hindleg in FIG. 11D before a destructive pulse.

Figure 12:
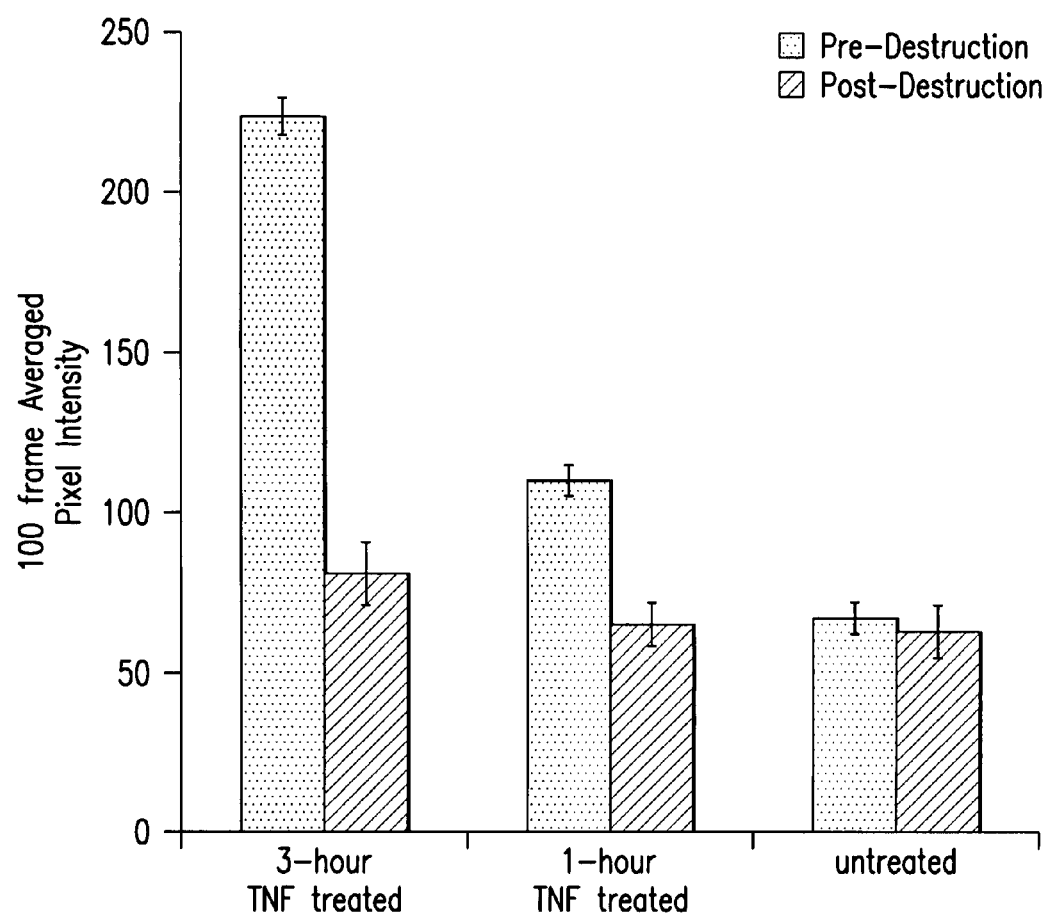
FIG. 12 shows pixel intensity within an ROI averaged over 100 frames before a destructive pulse and after MB destruction in inflamed and non-inflamed (untreated) hind leg. Error bars show standard deviation over 100 frames.

FIG. 12 shows pixel intensity within an ROI averaged over 100 frames before a destructive pulse and after MB destruction in inflamed and non-inflamed (untreated) hindleg. The error bars show standard deviation over 100 frames.

Example 3

Image Enhancement by Bolus Injection of Vascularized Tissue

A Vevo 770® (VisualSonics Inc. Toronto, Calif.) high-resolution imaging system was used to acquire data set images and reference set images. The Vevo® system included software for comparing, matching and subtracting data set images and reference set images. For example, Vevo® Contrast Mode software was used.

The Default Cine Loop Size for Contrast Mode was set at 800, which defined the size of the Contrast Mode cine loop. A high frequency ultrasound imaging probe was connected to the to the Vevo® 770 imaging system. In this example, an RMV™-706 probe (VisualSonics Inc., Toronto, Calif.) was used.

The subject was positioned for scanning, and while scanning, the Field of View was adjusted to be 9×9 mm. Images were acquired at a frame rate between 10 and 20 Hz and the transmit power was set to 50%.

Contrast agent was prepared according to the instructions provided in VisualSonics, Inc. (Toronto, Calif.) Preparation Protocol—Preparation for Bolus Injection using the Vevo MicroMarker™ Contrast Agent Kits.

The MicroMarker™ Microbubbles, made by Bracco Research SA (Amsterdam, Netherlands) and available from VisualSonics (Toronto, Calif.), were used for improved vascular enhancement and perfusion imaging. MicroMarker™ Microbubbles are lyophilized microbubbles with a lipid based shell containing polyethylene Glycol, Phospholipids and fatty acid. The bubbles are stored in a glass vial containing a gas head consisting of nitrogen and perfluorobutane gas. The Microbubbles will become gas filled contrast enhancing agents when reconstituted with saline, agitated and allowed to incubate for 10 mins.

The Vevo MicroMarker™ Contrast Agent Kits were used to prepare the microbubble agent in order to observe image enhancement due to the introduction of the contrast agent at the fundamental imaging frequency. Upon bolus injection, opacification of larger vessels were demonstrated with gradual infiltration of contrast into the anatomical area of interest.

The MicroMarker™ solution was prepared for Mouse Imaging using a 1 ml syringe pre-filled with 0.7 ml of sterile saline. A 21 G ⅝" needle was attached and the sterile saline was injected into the MicroMarker™ vial. The syringe was removed and the needle was left to vent before removal of the needle. The vial was gently agitated hand for one minute and then the vial was allowed to rest for 10 minutes. A 27 G ½" needle was attached to a 1 ml syringe pre-filled with sterile saline to be used as a flush syringe.

An empty 1 ml syringe and a second 21 G ⅝" needle was used to draw up approximately 120 µL of prepared MicroMarker™ from the vial to compensate for the dead space in the needle hub. The vial was gently agitated in a top-to-bottom manner before collecting a sample. The air that is drawn up as well was removed and the volume was adjusted to 50 µl. This was the bolus amount used for injection.

The reconstituted MicroMarker™ vial contained $2\times10^9$ microbubbles/ml. A 50 μL bolus was delivered using a 27½ G needle to give a final working solution of $1.0\times10^8$ microbubbles for imaging most tumors and less vascularized areas like the hind limb.

The Microbubbles can be further diluted with saline in order to perform a dose response curve or to determine the optimal number of microbubbles. For example, $1.0\times10^7$ microbubbles/50 μl can be used for well vascularized tissues such as the kidney and liver. This can be achieved by performing a 1:10 dilution of the original stock concentration. For each injection a 1:10 dilution of the stock solution includes 15 μL of contrast agent to be diluted to 150 μL with saline (i.e. add 15 μL of contrast agent to 135 μL of saline). The dilution can be performed immediately before the injection is to be delivered in order to avoid destabilization of the microbubbles. Any additional contrast agent removed from the vial can be discarded.

Bolus injection of Microbubbles can follow the following protocols depending on the area of interest. For tumors: $1\times10^8$ bubbles/50 μL bolus; for the Retina (eye): $1\times10^8$ bubbles/50 μl bolus; for cardiovascular: $1\times10^7$ bubbles/50 μl bolus; for the liver: $1\times10^7$ bubbles/50 μl bolus; for the hind limb (muscle): $1\times10^8$ bubbles/50 μl bolus.

A small animal subject was prepared for imaging. Contrast agent was injected via tail vein, jugular vein or into a retro-orbital sinus. An appropriate imaging plane with the target to be imaged was centered inside the focal zone and an 800 frame baseline or reference set cine loop was acquired.

Another acquisition of an 800 frame data set image cine loop was started and a bolus of contrast agent was slowly and gently injected into the subject. The injection took about 5 seconds. Care was taken to inject the bolus slowly to avoid destruction of the microbubbles in the administered contrast agent. Acquisition stopped after 800 frames were acquired.

The Vevo 770, including the contrast mode feature and software, was used to process the acquired Contrast Mode data by comparing the acquired data set image cine loop with the selected images of the reference frames from the reference set cine loop. A "contrast overlay" or enhanced ultrasound image was created to identify the differences in image intensity between the reference and the data loops. This overlay represented the change in B-mode imaging caused by injection of the MicroMarker™ contrast agent.

To generate a contrast overlay the bolus-injection or data image set cine was loaded into the processing system of the Vevo® imaging system. A reference cine loop was created by selecting the first 25-100 frames from the loop during which no contrast agent has entered in the imaging plane. Persist options to apply the contrast overlay were selected based on the desired imaging protocol. For example, no filters were applied to visualize the movement of microbubbles with in the tissue. A smoothing filter was used to suppress moving microbubbles, which was useful in observing adherent bubbles by applying a 7 frame average display. MIP (Maximum Intensity Persistence) was used to show the track of the microbubbles through the vascular structure by using a subtracted display that averages frames together.

Figure 13:
FIG. 13 shows a contrast region measurement created using exemplary methods of creating an enhanced medical image.
Figure 14:
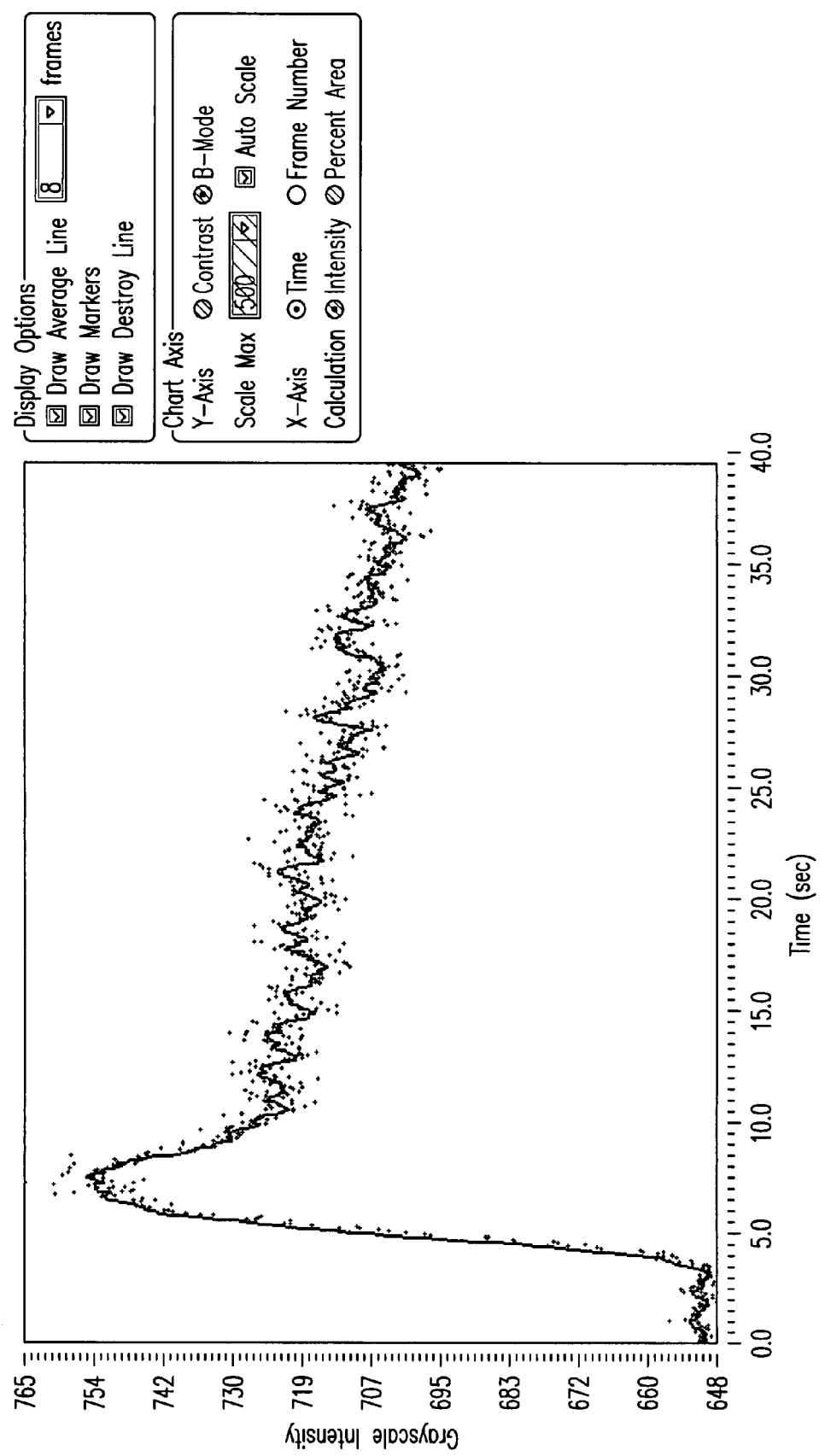
FIG. 14 shows a contrast region intensity curve vs time graph created using data obtained from an enhanced medical image created using the exemplary methods described herein.

The acquired Contrast Mode data was analyzed. The processed bolus-injection cine loop to be analyzed was loaded into the Vevo processing system. A contrast region measurement was created as shown in FIG. 13. To create the contrast region measurement, measurement calipers were used to trace the edge of the tissue. A contrast region intensity curve vs time graph was also create as shown in FIG. 14.

Example 4

A Vevo 770® (VisualSonics Inc. Toronto, Calif.) high-resolution imaging system was used to acquire data set images and reference set images. The Vevo® system included software for comparing, matching and subtracting data set images and reference set images. For example, Vevo® Contrast Mode software was used.

The Default Cine Loop Size for Contrast Mode was set at 800, which defined the size of the Contrast Mode cine loop. A high frequency ultrasound imaging probe was connected to the to the Vevo® 770 imaging system. In this example, an RMV™-706 probe (VisualSonics Inc., Toronto, Calif.) was used. The transmit power was set to 100% and the maximum available frame rate was selected.

The contrast agent was prepared according to the instructions provided in the appropriate VisualSonics Inc. (Toronto, Calif.) Preparation Protocol.

The MicroMarker™ Ultrasound Contrast agents are made by Bracco Research SA (Amsterdam, Netherlands) for improved vascular enhancement imaging and are available from VisualSonics Inc. (Toronto, Calif.). DEPO™ MicroMarker™ agents are lyophilized microbubbles with a lipid based shell containing polyethylene glycol, phospholipids and fatty acids. The agents are stored in a glass vial containing a gas head-space consisting of nitrogen and perfluorobutane. The microbubbles are gas filled agents when reconstituted with saline. MicroMarker™ DEPO™ Kits can be stored at room temperature and have a shelf life of 6 months. The DEPO™ contrast agents that have been opened and reconstituted are stable within the vials for 4-6 hrs The DEPO™ agents were used to observe image enhancement of the myocardium due to the introduction of the contrast agent at the fundamental imaging frequency that lodges in the capillaries. Upon bolus injection, opacification of larger vessels was demonstrated with gradual infiltration of contrast into the structure/tissue.

DEPO™ MicroMarker™ Contrast Agent was prepared for Mouse Imaging. 1.4 ml of sterile saline was injected into the DEPO™ contrast agent vial using a prefilled syringe containing 0.7 ml of sterile saline and a 21 G ⅝" needle. The syringe was removed first to allow for ventilation, and then the needle was removed. The glass vial was gently agitated by hand for approx. 10 seconds and then left to rest for 10 minutes. A 27 G ½" needle was attached to a 1 ml syringe pre-filled with sterile saline to be used as a flush syringe.

The vial was gently agitated in a top to bottom manner to allow for even mixing. Using an empty 1 ml syringe and a second 21 G ⅝" needle, 90 μL of prepared DEPO™ contrast agent was drawn up from the vial. A 50 μL bolus from this amount was injected. The 21 G ⅝" needle was replaced with the second 27 G ½" needle and air was removed air for the injection.

A 50 μL bolus provided a final count of $1.2\times10^7$ microbubbles. The microbubbles can be further diluted with saline in order to perform a dose response curve or to determine the optimal number of microbubbles for a specific model. For example, a 1:2 dilution yields $6\times10^6$ bubbles/50 μL, which provides good results. Dilutions with adequate and gentle mixing can be performed in an eppendorf tube immediately prior to an injection into the animal, to minimize microbubble destabilization.

A small animal subject was prepared for imaging. Contrast agent was injected via tail vein, jugular vein or into a retro-orbital sinus.

An appropriate imaging plane with the target to be imaged was centered inside the focal zone and an 800 frame cine loop acquisition was begun. A bolus was slowly and gently injected into the subject. The injection took about 5 seconds. Injecting the bolus too quickly can destroy the contrast agent. Acquisition stops after 800 frames have been acquired. A second cine loop is acquired approximately 11 minutes after the final injection. This cine loop is compared during processing against the loop baseline saved initially to visualize areas enhanced by DEPO™ contrast agent.

The acquired cine loops including reference set images and data set images were compared and a "contrast overlay" was created to identify the differences in image intensity between these two loops. To generate a contrast overlay the baseline cine loop in which the injection occurred was identified as a reference cine loop. The cine loop acquired approximately 11 minutes after the final injection was used as the data cine loop. 11 minutes after DEPO™ injection, the ventricle was clear of circulating bubbles, and the myocardium became clearly defined, with the microbubbles deposited in areas where there is blood flow.

The Vevo MicroMarker Depo™ Contrast Agent Kits enable for the assessment of relative spatial perfusion of the myocardium in the mouse heart using a single intravenous contrast agent injection and the Vevo® 770 micro-ultrasound system. Using the MicroMarker™ Depo™ kit, mouse models of myocardial viability and left ventricular remodeling were analyzed.

MicroMarker™ Contrast Agent Characteristics

Vevo® MicroMarker™ is a contrast agent optimized for small animal micro-ultrasound imaging. It has been specifically developed for use on small animals using high frequency micro-ultrasound (>20 MHz). After reconstitution, the contrast agent contains gas-filled micro-bubbles that are administered intravenously to the subject. Ultrasound-based micro-bubbles are confined to the vascular compartment and provide strong reflections of the sound waves thereby providing detailed imaging of the blood circulation using the Vevo® 770. Due to the size distribution of the micro-bubbles in the MicroMarker™ DEPO™ contrast agent, a population of sufficiently large micro-bubbles evade pulmonary vascular filtering and are entrapped in the microvessels of the myocardium. The retention (or deposition) of the micro-bubbles in the myocardium is primarily due to lodging of a fraction of "large" (>5 µm) micro-bubbles.

The MicroMarker™ DEPO™ formulation used included a gas mixture of nitrogen and perfluorobutane and an excipient or polyethylene glycol, phospholipids, fatty acid and surfactant. The solvent used was sodium chloride 0.9% w/v in water.

The excipient constituents were contained in a lyophilized powder. After the micro-bubbles were reconstituted in saline and the vial was agitated, the micro-bubbles were then administered through the animal's venous system. These micro-bubbles contained a gas mixture and were stabilized by a phospholipid monolayer. The median diameter in volume of the administered micro-bubbles was approximately 5 µm.

Myocardial assessment using the MicroMarker™ DEPO™ contrast agent was performed in real-time with the full analysis workflow being completed in less than 20 minutes. The protocol used included DEPO™ contrast agent preparation, animal preparation (anesthetize animal, remove hair from area of imaging when required, gain vascular access for introduction of agent), imaging and acquiring baseline cineloop of myocardium (typically short axis view), injection of 50 µL bolus of DEPO™ contrast agent, imaging and acquiring cineloop of bolus injection, and acquiring a cineloop of myocardium opacification after waiting 10 minutes where the DEPO™ contrast agent has lodged in the microvessels.

Figure 15:
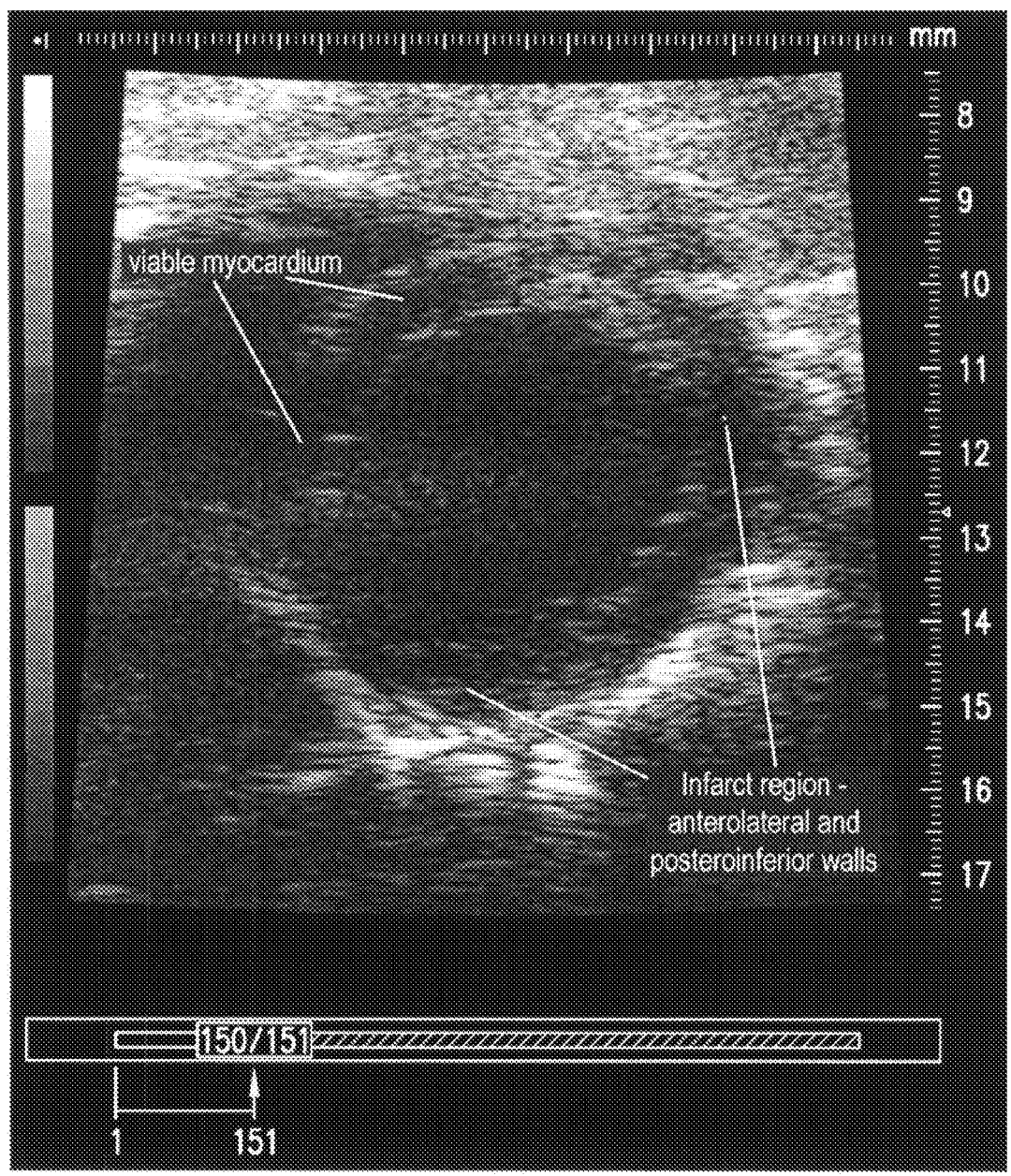
FIG. 15 shows a baseline image prior to DEPO™ bolus injection. Infarct regions in the anterolateral and posterolateral walls are illustrated as is the area of viable myocardium.
Figure 16:
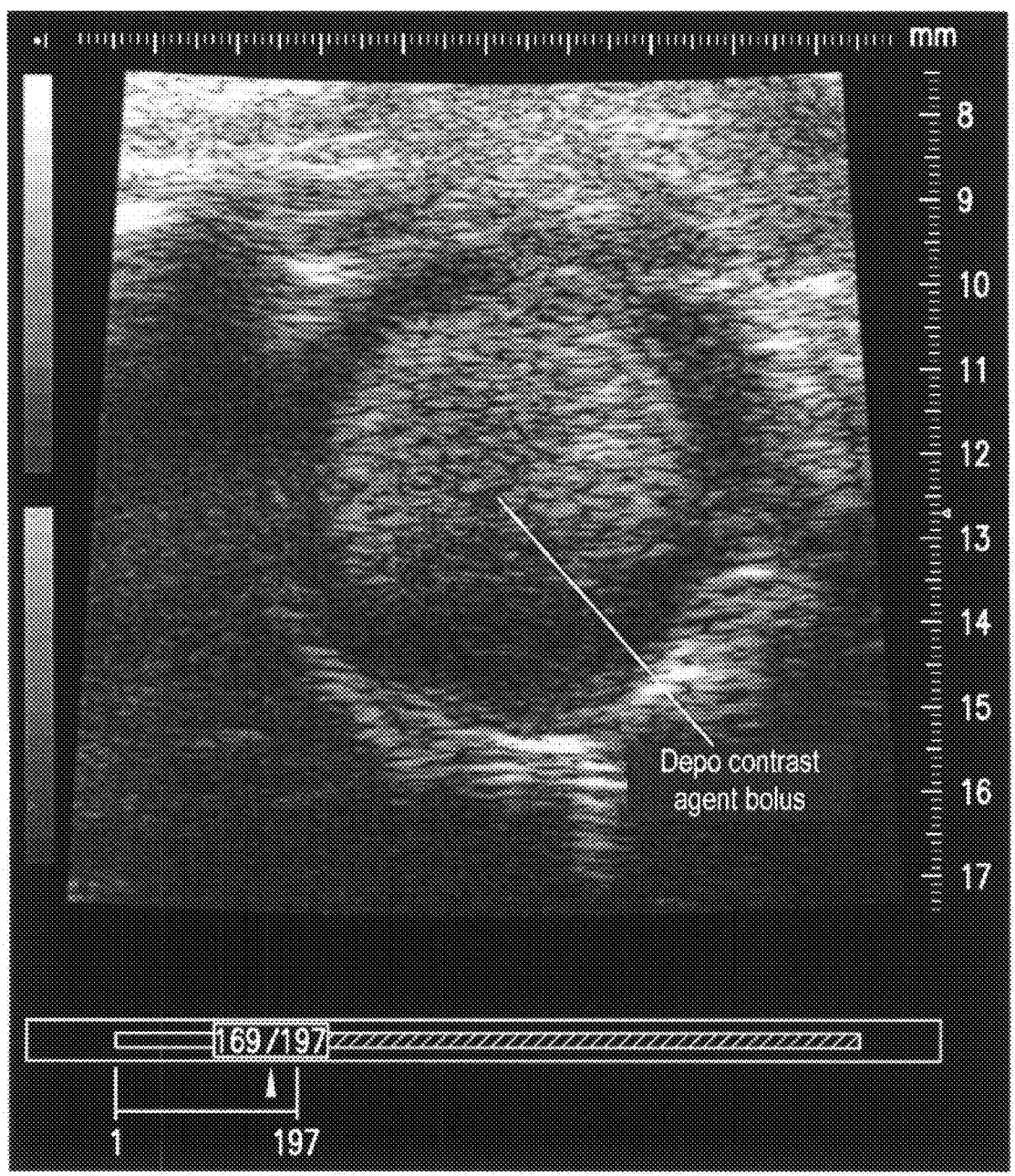
FIG. 16 shows an image of initial bolus injection as the left ventricular cavity is filled with DEPO™ contrast agent.
Figure 17:
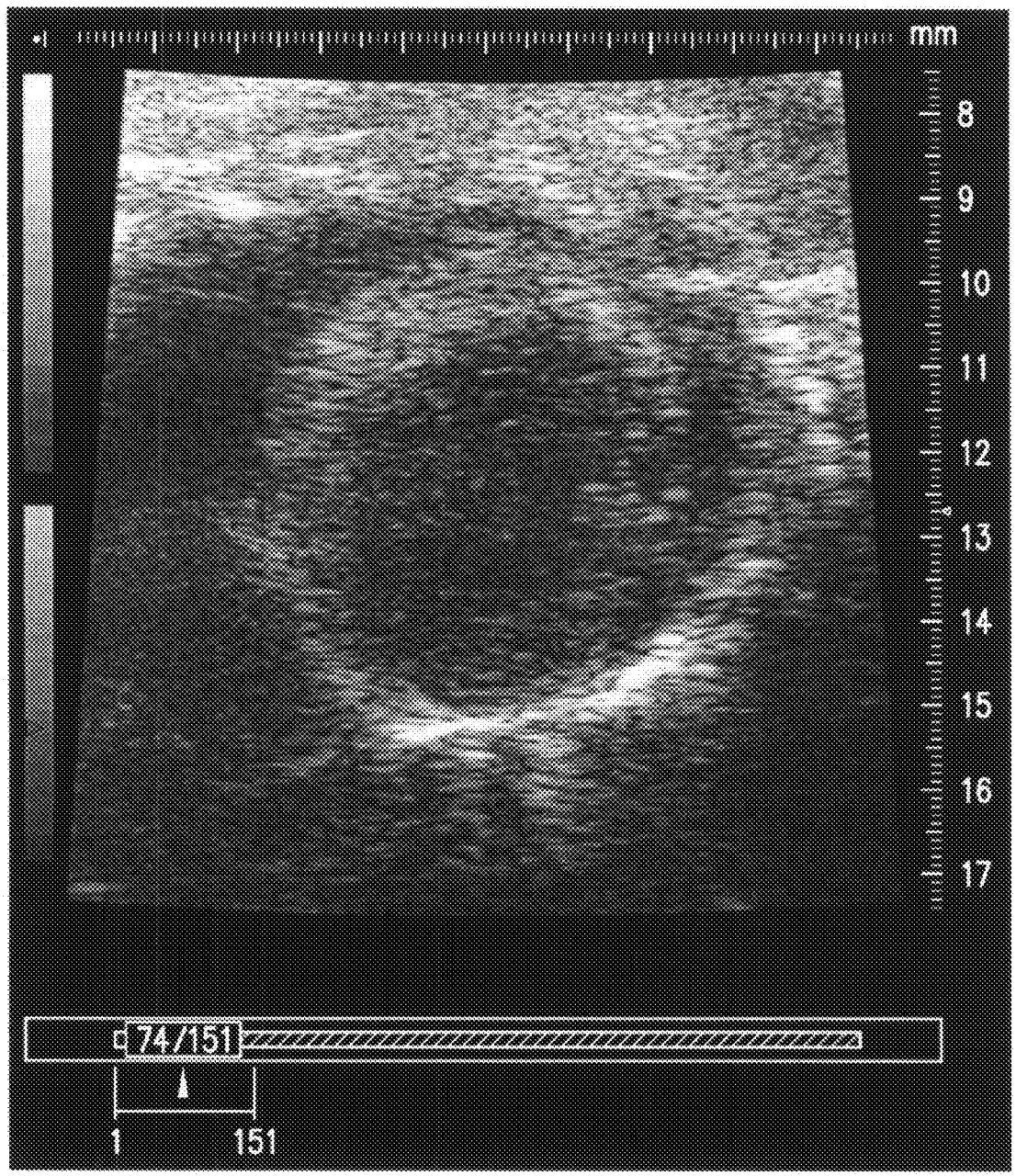
FIG. 17 shows an image of the left ventricle 10 minutes following injection of DEPO™. The DEPO™ contrast agent has perfused into the viable myocardial microcirculation and has cleared the left ventricular cavity.
Figure 18:
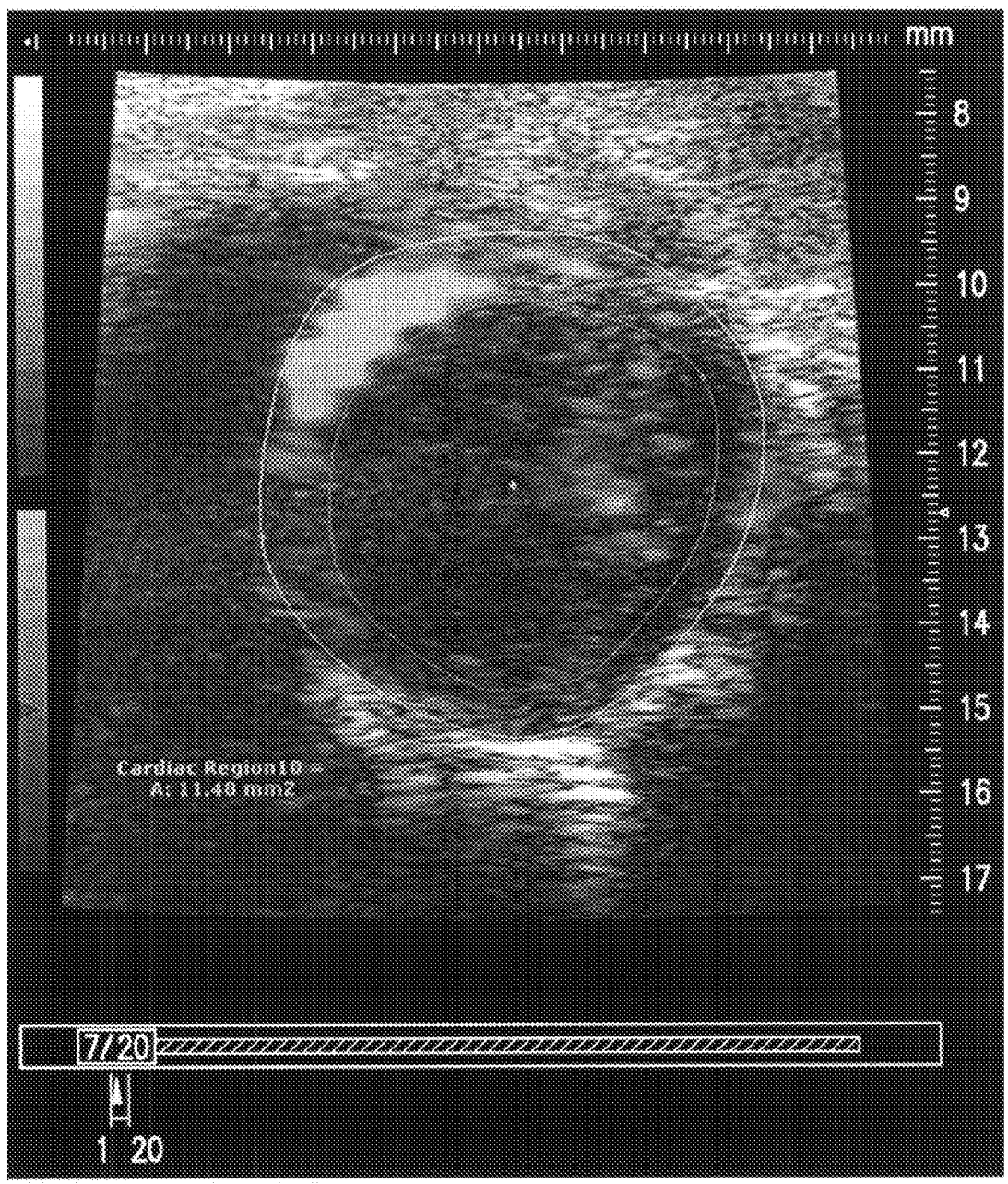
FIG. 18 shows a processed image showing the myocardial infarction using the DEPO™ data; the overlay indicates regions of well perfused myocardium and areas without the overlay indicate areas of myocardial infarction and tissue damage.
Figure 19:
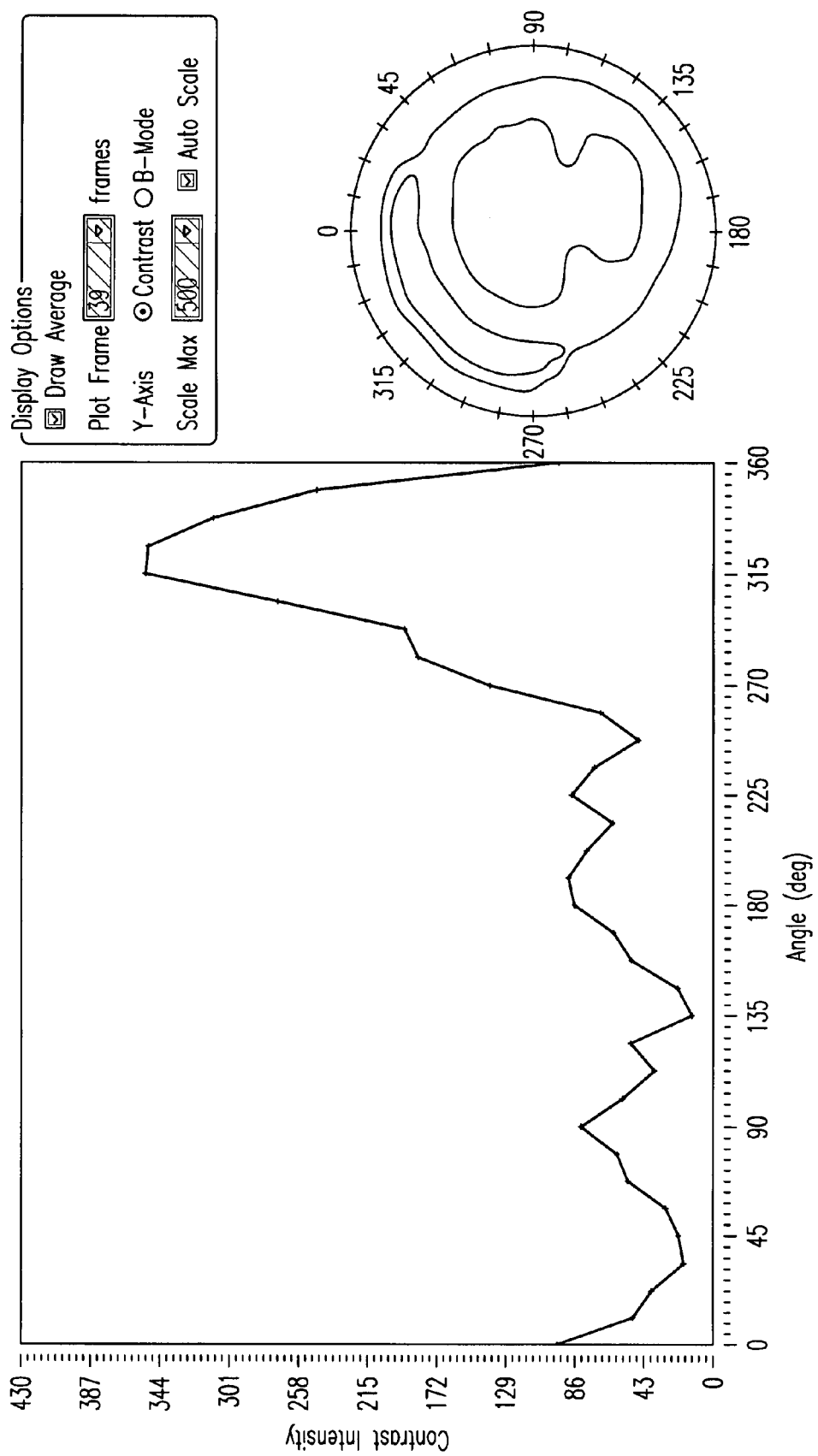
FIG. 19 shows a polar coordinate graph of processed images demonstrating the location of the region of infarction. Strong image intensity (y-axis) indicates viable myocardium and conversely low signal intensity illustrates damaged myocardial tissue.

FIG. 15 shows a baseline image prior to DEPO™ bolus injection. Infarct regions in the anterolateral and posterolateral walls are illustrated as is the area of viable myocardium. FIG. 16 shows an image of initial bolus injection as the left ventricular cavity is filled with DEPO™ contrast agent. FIG. 17 shows an image of the left ventricle 10 minutes following injection of DEPO™. The DEPO™ contrast agent has perfused into the viable myocardial microcirculation and has cleared the left ventricular cavity. FIG. 18 shows a processed image showing the myocardial infarction using the DEPO™ data; the overlay indicates regions of well perfused myocardium and areas without the overlay indicate areas of myocardial infarction and tissue damage. FIG. 19 shows a polar coordinate graph of processed images demonstrating the location of the region of infarction. Strong image intensity (y-axis) indicates viable myocardium and conversely low signal intensity illustrates damaged myocardial tissue.

Throughout this application, various publications are referenced. The disclosures of these publications in their entireties are hereby incorporated by reference into this application in order to more fully describe the state of the art to which this invention pertains.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of producing an enhanced medical image of a subject, comprising:
   producing a reference set of medical images of a subject or a portion thereof using a medical imaging modality, wherein the reference set of medical images comprises a plurality of reference set images;
   producing a data set of medical images of the subject or a portion thereof using the medical imaging modality, wherein the data set of medical images comprises a plurality of data set images, each data set image comprising data received from an area of increased contrast;
   comparing each of a plurality of the data set images to each of a plurality of the reference set images to identify a data-reference image pair, wherein the identified data-reference image pair comprises the reference set image that has the smallest difference error as to the data set image versus the other compared reference set images; and subtracting the identified reference image of the data-reference image pair from the data image of the data-reference image pair to create the enhanced medical image, wherein each reference set image of the reference set is acquired from a portion of the subject undergoing dynamic motion during the acquisition, and each data set image of the data set is acquired from a portion of the subject undergoing dynamic motion during the acquisition, and wherein the area of increased contrast is not created in the subject when the reference images are produced.

2. The method of claim 1, wherein the area of increased image contrast in the subject is created by increasing the intensity of the image in the area.

3. The method of claim 1, wherein the area of increased image contrast in the subject is created by decreasing the intensity of the image in the area.

4. The method of claim 1, wherein producing a data set of medical images comprises obtaining images from an area in which a medical imaging contrast agent has been administered to the subject.

5. The method of claim 4, wherein the contrast agent is selected from the group consisting of: ultrasound imaging contrast agent, computed tomography imaging contrast agent, optical imaging contrast agent, magnetic resonance imaging contrast agent, optical coherence tomography imaging contrast agent, radiography imaging contrast agent, nuclear medical imaging contrast agent, positron emission tomography imaging contrast agent, tomography imaging contrast agent, thermal imaging contrast agent, fluoroscopy imaging contrast agent, bioluminescent imaging contrast agent, and biofluorescent imaging contrast agent.

6. The method of claim 5, wherein the medical imaging modality is ultrasound and the ultrasound imaging contrast agent is a microbubble contrast agent.

7. The method of claim 1, wherein the creation of the area of increased contrast and the production of the data set of medical images occur prior to the production of the reference set of medical images.

8. The method of claim 1, wherein the medical imaging modality is selected from the group consisting of ultrasound, computed tomography, optical imaging, magnetic resonance imaging, optical coherence tomography, radiography, nuclear medical imaging, positron emission tomography, tomography, thermal imaging, fluoroscopy, bioluminescent imaging, and biofluorescent imaging.

9. The method of claim 8, wherein the medical imaging modality is a high frequency ultrasound imaging system that can transmit ultrasound using a transducer having a center transmit frequency of at least about 15 megahertz (MHz).

10. The method of claim 9, wherein the high frequency ultrasound imaging system can transmit ultrasound using a transducer having a center transmit frequency of between about 15 MHz and about 100 MHz.

11. The method of claim 10, wherein the high frequency ultrasound imaging system can transmit ultrasound using a transducer having a center transmit frequency of between about 20 MHz and about 60 MHz.

12. The method of claim 1, wherein the medical images are 3-Dimensional medical images.

13. The method of claim 1, wherein each reference set image of the reference set is acquired sequentially and wherein each data set image of the data set is acquired sequentially.

14. The method of claim 1, wherein the difference error is determined by processing the data image and the reference image to determine a sum of the absolute difference of intensity levels between pixels of the data image and pixels of the reference image.

15. The method of claim 1, wherein the difference error is determined by processing the data image and the reference image to determine a sum difference of intensity levels between pixels of the data image and pixels of the reference image.

16. The method of claim 1, wherein the difference error is determined by processing the data image and the reference image to determine a difference of intensity level between the data image and the reference image.

17. The method of claim 1, wherein the difference error is determined by a correlation technique that determines a difference of intensity level between the data image and the reference image.

18. The method of claim 1, wherein the difference error is determined by determining the sum of the absolute difference of pixels between the data image and the reference image.

19. The method of claim 1, wherein the difference error is determined by a method selected from the group consisting of correlation techniques, frequency domain techniques, and pattern matching techniques.

20. The method of claim 1, wherein subtracting the reference image and the data image comprises subtracting the pixel intensities of the reference image from the pixel intensities of the data image.

21. The method of claim 1, further comprising comparing a plurality of data set images to a plurality of reference set images and identifying a plurality of data-reference image pairs.

22. The method of claim 21, further comprising processing the plurality of data-reference image pairs to create a plurality of enhanced medical images.

23. The method of claim 22, further comprising processing the plurality of enhanced medical images to create a persisted enhanced medical image.

24. The method of claim 23, wherein the processing of the plurality of enhanced images comprises taking a moving average of the plurality of enhanced images to create the persisted enhanced medical image.

25. The method of claim 1, further comprising pre-processing the data image and the reference image of an identified data-reference image pair prior to subtracting the reference image of the data-reference image pair from the data image of the data-reference image pair to create the enhanced medical image.

26. The method of claim 25, wherein the pre-processing is selected from the group consisting of decimation, filtration, noise reduction filtration, contrast enhancement filtration, blurring filtration, low pass filtration, high pass filtration, non-linear filtration, median filtration, maximum filtration, averaging filtration, mean filtration, mode filtration, Monte Carlo filtration, box filtration, Gaussian filtration, histogram equalization filtration, linear image transformation, resizing, rotation, shifting, non-linear transformations, and imaging morphing.

27. The method of claim 1, further comprising displaying the enhanced medical image over the data image used in the data-reference image pair.

28. The method of claim 1, further comprising displaying the enhanced medical image over the reference image used in the data-reference image pair.

29. The method of claim 1, wherein the subject is a small animal.

30. The method of claim 1, wherein each data image and each reference image are identified temporally with respect to a biodynamic cycle of the subject.

31. The method of claim 30, wherein the biodynamic cycle is a cardiac cycle or respiratory cycle of the subject.

32. The method of claim 30, further comprising selecting a data set image having a given temporal identity with respect to the biodynamic cycle for comparison to the reference set Images.

33. The method of claim 30, further comprising identifying a subset of reference set images based on the temporal identity of each reference set image of the subset with respect to the biodynamic cycle of the subject, wherein each reference set image of the subset has a proximal relative temporal identity with respect to the biodynamic cycle compared to the temporal identity of the data set image, and wherein the plurality of reference images to be compared to the data set image to identify a data-reference pair is selected from the subset of reference images.

34. The method of claim 31, wherein the data image and the reference image in a given data-image pair each have a temporal identifier indicating that the paired images were captured at a similar phase of a cardiac or respiratory cycle of the subject.

35. A method of producing an enhanced medical image of a subject, comprising:
   producing a reference set of medical images of a subject or a portion thereof using a medical imaging modality, wherein the reference set of medical images comprises a plurality of reference set images;
   producing a data set of medical images of the subject or a portion thereof using the medical imaging modality, wherein the data set of medical images comprises a plurality of data set images, each data set image comprising contrast image data received from an area of increased contrast in the subject;
   comparing each of a plurality of the data set images to each of a plurality of the reference set images to identify a data-reference image pair having a smallest difference error between the compared data set image and reference set image; and
   subtracting the reference image of the data-reference image pair from the data image of the data-reference image pair to create the enhanced medical image, wherein each reference set image of the reference set is acquired from a portion of the subject undergoing dynamic motion during the acquisition, and each data set image of the data set is acquired from a portion of the subject undergoing dynamic motion during the acquisition, and wherein the area of increased contrast is not created in the subject when the reference images are produced.

36. The method of claim 35, wherein the creation of the area of increased contrast comprises administering a medical imaging contrast agent to the subject.

37. The method of claim 35, wherein the creation of the area of increased contrast and the production of the data set of medical images occur prior to the production of the reference set of medical images.

38. The method of claim 35, wherein areas of substantial similarity are determined by processing the data image and the reference image to determine a sum of the absolute difference of intensity levels between pixels of the data image and pixels of the reference image.

39. The method of claim 35, wherein areas of substantial similarity are determined by processing the data image and the reference image to determine a sum of the difference of intensity levels between pixels of the data image and pixels of the reference image.

40. The method of claim 35, wherein areas of substantial similarity are determined by processing the data image and the reference image to determine a difference of intensity level between the data image and the reference image.

41. The method of claim 35, further comprising pre-processing the data image and the reference image of an identified data-reference image pair prior to subtracting the reference image of the data-reference image pair from the data image of the data-reference image pair to create the enhanced medical image.

42. The method of claim 35, wherein each data image and each reference image are identified temporally with respect to a biodynamic cycle of the subject.

43. The method of claim 42, wherein the biodynamic cycle is a cardiac cycle or respiratory cycle of the subject.

44. The method of claim 42, further comprising selecting a data set image having a given temporal identity with respect to the biodynamic cycle for comparison to the reference set images.

45. The method of claim 44, further comprising identifying a subset of reference set images based on the temporal identity of each reference set image of the subset with respect to the biodynamic cycle of the subject, wherein each reference set image of the subset has a proximal relative temporal identity with respect to the biodynamic cycle compared to the temporal identity of the data set image, and wherein the plurality of reference images to be compared to the data set image to identify a data-reference pair is selected from the subset of reference images.

46. The method of claim 43, wherein the data image and the reference image in a given data-image pair each have a temporal identifier indicating that the paired images were captured at a similar phase of a cardiac or respiratory cycle of the subject.

47. A method of producing an enhanced medical image of a subject, comprising:
   producing a reference set of medical images of a subject or a portion thereof using a medical imaging modality, wherein the reference set of medical images comprises a plurality of reference set images and wherein the reference medical images comprise data received from the subject's tissue;
   producing a data set of medical images using the medical imaging modality, wherein the data set of medical images comprises a plurality of data set images, and wherein the data set of medical images comprises contrast data received from a medical imaging contrast agent administered to the subject and data received from the subject's tissue;
   comparing each of a plurality of the data set images to each of a plurality of the reference set images to identify a data-reference image pair, wherein the data-reference image pair is identified based on having a smallest difference error between the tissue data of the reference image relative to the tissue data of the data image; and
   determining the difference between the reference image and the data image of the data-reference image pair to create the enhanced medical image, wherein each reference set image of the reference set is acquired from a portion of the subject undergoing dynamic motion during the acquisition, and each data set image of the data set is acquired from a portion of the subject undergoing dynamic motion during the acquisition, and wherein an area of increased contrast is not created in the subject when the reference images are produced.

48. The method of claim 47, wherein the similarity of tissue data of the reference image relative to the tissue data of the data image is determined by processing the data image and the reference image to determine a sum of the absolute difference of intensity levels between pixels of the data image and pixels of the reference image.

49. The method of claim 47, wherein the similarity of tissue data of the reference image relative to the tissue data of the data image is determined by processing the data image and the reference image to determine a sum of the difference of intensity levels between pixels of the data image and pixels of the reference image.

50. The method of claim 47, wherein the similarity of tissue data of the reference image relative to the tissue data of the data image is determined by processing the data image and the reference image to determine a difference of intensity level between the data image and the reference image.

51. The method claim 47, wherein determining the difference between the reference image and the data image comprises subtracting the pixel intensities of the reference image from the pixel intensities of the data image.

52. The method of claim 51, further comprising pre-processing the data image and the reference image of an identified data-reference image pair prior to determining the difference between the reference image of the data-reference image pair from the data image of the data-reference image pair to create the enhanced medical image to create the enhanced medical image.

53. The method of claim 47, wherein each data image and each reference image are identified temporally with respect to a biodynamic cycle of the subject.

54. The method of claim 53, further comprising selecting a data set image having a given temporal identity with respect to the biodynamic cycle for comparison to the reference set images.

55. The method of claim 54, further comprising identifying a subset of reference set images based on the temporal identity of each reference set image of the subset with respect to the biodynamic cycle of the subject, wherein each reference set image of the subset has a proximal relative temporal identity with respect to the biodynamic cycle compared to the temporal identity of the data set image, and wherein the plurality of reference images to be compared to the data set image to identify a data-reference pair is selected from the subset of reference images.

56. The method of claim 55, wherein the data image and the reference image in a given data-image pair each have a temporal identifier indicating that the paired images were captured at a similar phase of a cardiac or respiratory cycle of the subject.

57. A method of producing an enhanced medical image of a subject, comprising:
producing a reference set of medical images of a subject or a portion thereof using a medical imaging modality, wherein the reference set of medical images comprises a plurality of reference set images;
producing a data set of medical images of the subject or a portion thereof using the medical imaging modality, wherein the data set of medical images comprises a plurality of data set images, each data set image comprising data received from an area of increased image contrast;
comparing each of a plurality of the data set images to each of a plurality of the reference set images;
determining the relative similarity between the data set image and each compared reference set image;
selecting a data-reference image pair, wherein the selected data-reference image pair comprises a data set image and a reference set image, and wherein the selected data-reference image pair has a smallest difference error between the data set image and the reference set image based on the reference image's determined relative similarity to the data image; and
processing the data-reference image pair to create the enhanced medical image by removing the areas of substantial similarity between the data image and the reference image of the data-reference image pair, wherein each reference set image of the reference set is acquired from a portion of the subject undergoing dynamic motion during the acquisition, and each data set image of the data set is acquired from a portion of the subject undergoing dynamic motion during the acquisition, and wherein the area of increased image contrast is not created in the subject when the reference images are produced.

* * * * *